United States Patent
Danishefsky et al.

(10) Patent No.: US 8,067,462 B2
(45) Date of Patent: Nov. 29, 2011

(54) PROCESSES OF MAKING SESQUITERPENOID TASHIRONIN, ITS ANALOGS AND THEIR USES

(75) Inventors: Samuel J. Danishefsky, Englewood, NJ (US); Silas P. Cook, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 732 days.

(21) Appl. No.: 11/793,646

(22) PCT Filed: Dec. 20, 2005

(86) PCT No.: PCT/US2005/046183
§ 371 (c)(1),
(2), (4) Date: Sep. 25, 2008

(87) PCT Pub. No.: WO2006/083417
PCT Pub. Date: Aug. 10, 2006

(65) Prior Publication Data
US 2009/0105332 A1   Apr. 23, 2009

Related U.S. Application Data

(60) Provisional application No. 60/637,927, filed on Dec. 20, 2004.

(51) Int. Cl.
*A61K 31/34* (2006.01)
*C07D 307/77* (2006.01)

(52) U.S. Cl. .................................. 514/468; 549/457

(58) Field of Classification Search .................. 514/468; 549/457
See application file for complete search history.

(56) References Cited

U.S. PATENT DOCUMENTS

| | | | |
|---|---|---|---|
| 6,936,714 | B2 | 8/2005 | Danishefsky et al. |
| 2003/0216397 | A1 | 11/2003 | Flores et al. |
| 2009/0105332 | A1 | 4/2009 | Danishefsky et al. |
| 2009/0131498 | A1 | 5/2009 | Danishefsky et al. |

OTHER PUBLICATIONS

PCT International Publication No. WO/2006/083417, published on Aug. 10, 2006.
International Search Report issued by the International Searching Authority (ISA/US) on Dec. 18, 2006 in connection with International Application No. PCT/US2005/046183.
Fukuyama, Y. et al., (1995) "Tashironin, A Plausible Biosynthetic Precursor of Anisatin-Type Sesquiterpenes," *Tetrahedron Letters*, 36(4): 583-586.
Schmidt, T.J. et al., (2001) "New *allo*-Cedrane Type Sesquiterpene Hemiketals and Further Sesquiterpene Lactones from Fruits of *Illicium floridanum*," *Journal of Natural Products*, 64: 411-414.
Huang, J. et al., (2001) "Structure and Neurotrophic Activity of *seco*-Prezizaane-Type Sesquiterpenes from *Illicium merrillianum*," *Journal of Natural Products*, 64: 428-431.
Huang, J. et al. (2002) "Brine Shrimp Lethality Test Active Constituents and New Highly Oxygenated *Seco*-prezizaane-Type Sesquiterpenes from *Illicium merrillianum*," *Chem. Pharm. Bull.* 50(1): 133-136.
Written Opinion of the International Searching Authority issued by the International Searching Authority (ISA/US) on Dec. 18, 2006 in connection with International Application No. PCT/US2005/046183.
PCT International Publication No. WO/2007/087220, published on Aug. 2, 2007.
PCT International Publication No. WO/2006/079112, published on Jul. 27, 2006.
PCT International Publication No. WO 03/051303, published on Jun. 26, 2006.
International Search Report in connection with PCT/US07/01329 published Nov. 8, 2007.
International Search Report in connection with PCT/US2006/002643 published Nov. 30, 2006.
International Preliminary Report on Patentability in connection with PCT/US2006/002643 issued Jul. 24, 2007.
International Preliminary Report on Patentability in connection with PCT/US2005/046183 issued Jun. 27, 2007.
Written Opinion in connection with PCT/US2006/002643 issued Jul. 24, 2007.
International Preliminary Report on Patentability in connection with PCT/US2007/001329 issued Jul. 29, 2008.
Written Opinion in connection with PCT/US2007/001329 issued Sep. 12, 2007.

*Primary Examiner* — Taofiq A Solola
(74) *Attorney, Agent, or Firm* — John P. White; Cooper & Dunham LLP

(57) ABSTRACT

A compound having the structure of the formula (genus of compound 1 excluding Tashironin or Debenzoyltashironin)

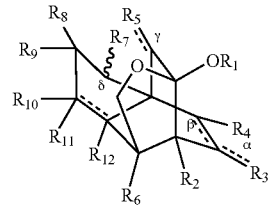

and methods of the same.

24 Claims, No Drawings

PROCESSES OF MAKING SESQUITERPENOID TASHIRONIN, ITS ANALOGS AND THEIR USES

This application is a §371 national stage of PCT International Application No. PCT/US2005/046183, filed Dec. 20, 2005, and claims the benefit of U.S. Provisional Application No. 60/637,927, filed Dec. 20, 2004, the contents of all of which are hereby incorporated by reference into this application.

This invention has been made with government support under National Institutes of Health grant HL25848. Accordingly, the U.S. Government has certain rights in the invention.

Throughout this application various publications are referenced in parenthesis. The disclosures of these publications in their entireties are hereby incorporated by reference into this application in order to more fully describe the state of the art to which this invention pertains.

BACKGROUND

Neurotrophic factors, or neurotrophins, are agents that can prevent neuronal death (neurotrophism) or promote axonal growth (neurotropism). To date, all widely studied neurotrophins (c.f. NGF, BDNF, GDNF, NT4/5, NT6) are naturally occurring polypeptides or proteins (Bennett, et al., *Auton. Neurosci.* 2002, 95, 1; Lu, et al., *J. Comp. Neurol.* 2001, 436, 456; Kaneko, *J. Med. Chem.* 1997, 40, 1863). Given their potential to treat neurodegenerative disorders, it is not surprising that neurotrophic factors have been the focus of considerable interdisciplinary research since the discovery of the first neurotrophin, NGF, by Montalcini and Hamburger (Levi-Montalcini, et al., *J. Exp. Zool.* 1951, 116, 321-362). Indeed, peptidyl neurotrophic factors have been extensively evaluated in animal models for their ability to treat neurodegenerative disease. However, due to unfavorable drug delivery and pharmacokinetic characteristics, in vivo evaluation of these neurotrophins requires direct microinjection into the brain (Kaneko, *J. Med. Chem.* 1997, 40, 1863; Kirik, et al., *Nature Neuroscience* 2004, 7, 105; Dawbarn, et al., *Neuropathology and Applied Neurobiology* 2003, 29, 211-30; Pollack, et al., *Curr. Drug Target CNS Neurol. Disord.* 2002, 1, 59; Gonzalez, et al., *Brain Res.* 2001, 920, 65; Fournier, *J. Pharm. Pharmacol.* 1998, 50, 323). Clearly, drug availability problems associated with these polypeptidic structures are a serious impediment to their development in prospective human settings.

In 1995, Fukayama, Shida, and Kodama reported the isolation and structural characterization of the neurotrophically inactive sesquiterpenoid tashironin (2) from the wood of *illicium tashiroi* (Fukuyama, et al., *Tetrahedron Lett.* 1995, 36, 583). More recently, Fukuyama and coworkers reported on the isolation and structure elucidation of 11-O-debenzoyltashironin (1), which promotes neurite growth at concentrations as low as 0.1 μmol. (Huang, et al., *J. Nat. Prod.* 2001, 64, 428).

Structure of Debenzoyltashironin 1 and Tashironin 2

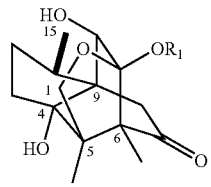

$R_1$ = H: Debenzoyltashironin (1)
$R_1$ = Bz: Tashironin (2)

SUMMARY OF THE INVENTION

The subject application provides for a compound having the structure of the formula (72)

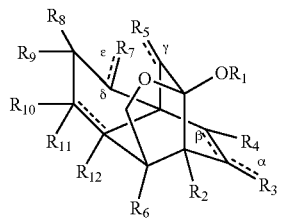

wherein, $R_1$ is H or Bz when no more than three of $R_8$, $R_9$, $R_{10}$ and $R_{11}$ are H, or $R_1$ is Bn, ($C_1$-$C_4$) alkyl, or $CF_3$;

$R_2$ is H, ($C_1$-$C_4$) alkyl, halide, OC(O)($C_1$-$C_4$)alkyl, OC(O)Ph, or OCF$_3$;

$R_3$ is p-toluene sulfonyloxy, methane sulfonyloxy, C(O)($C_1$-$C_4$)alkyl, or OC(O)($C_1$-$C_4$)alkyl, bond α is a single bond, and bond β is a double bond or $R_3$ is O, bond α is a double bond and bond β is a single bond;

$R_4$ is H, I, Br, Cl, Si(CH$_3$)$_3$, ($C_1$-$C_4$)alkyl, or OCF$_3$;

$R_5$ is OH, OSi(CH$_3$)$_3$, O($C_1$-$C_4$) alkyl, or OCF$_3$, and bond γ is a single bond, or $R_5$ is O and bond γ is a double bond;

$R_6$ is H, ($C_1$-$C_4$) alkyl, or CF$_3$;

$R_7$ is H, OH, ($C_1$-$C_4$)alkyl, CH$_2$OBn, CH$_2$O($C_1$-$C_4$)alkyl, CH$_2$OH, halide, CH$_2$OCF$_3$ or OCF$_3$ and bond ε is a single bond, or $R_7$ is CH$_2$ and bond ε is a double bond;

$R_8$, $R_9$, and $R_{10}$ are each independently H, ($C_1$-$C_4$)alkyl, halide, OH, or OCF$_3$;

$R_{11}$ is H, ($C_1$-$C_4$)alkyl, halide, OH, or OCF$_3$ and bond δ is a single bond;

$R_{12}$ is H, ($C_1$-$C_4$)alkyl, O($C_1$-$C_4$)alkyl, p-toluene sulfonyloxy or methane sulfonyloxy, halide, OH, OCF$_3$, or $R_{15}R_{16}$Si, where $R_{15}$ and $R_{16}$ are each independently ($C_1$-$C_4$)alkyl, furanyl or Ph, and bond δ is a single bond;

$R_{11}$ together with $R_{12}$ and the carbons to which each is attached to form an oxirane moiety form an ether group and bond δ is a single bond; or $R_{11}$ and $R_{12}$ are absent and bond δ is a double bond.

The subject application also provides for a compound having the structure of the formula (63)

wherein $R_{13}$ is C(O)OH, C(O)O($C_1$-$C_4$)alkyl, or C(O)S($C_1$-$C_4$)alkyl.

The subject application also provides for a composition comprising a compound having the structure of the formula (72)

wherein,
$R_1$ is H, Bn, Bz, ($C_1$-$C_4$)alkyl, or $CF_3$,
$R_2$ is H, ($C_1$-$C_4$) alkyl, halide, OC(O)($C_1$-$C_4$)alkyl, OC(O)Ph, or $OCF_3$;
$R_3$ is p-toluene sulfonyloxy, methane sulfonyloxy, C(O)($C_1$-$C_4$)alkyl, or OC(O)($C_1$-$C_4$)alkyl, bond α is a single bond, and bond β is a double bond or
$R_3$ is O, bond α is a double bond and bond β is a single bond;
$R_4$ is H, I, Br, Cl, Si($CH_3$)$_3$, ($C_1$-$C_4$)alkyl, or $OCF_3$;
$R_5$ is OH, OSi($CH_3$)$_3$, O($C_1$-$C_4$) alkyl, or $OCF_3$, and bond γ is a single bond, or
$R_5$ is O and bond γ is a double bond;
$R_6$ is H, ($C_1$-$C_4$) alkyl, or $CF_3$;
$R_7$ is H, OH, ($C_1$-$C_4$)alkyl, $CH_2$OBn, $CH_2$O($C_1$-$C_4$)alkyl, $CH_2$OH, halide, $CH_2OCF_3$ or $OCF_3$ and bond ε is a single bond, or
$R_7$ is $CH_2$ and bond ε is a double bond;
$R_8$, $R_9$, and $R_{10}$ are each independently H, ($C_1$-$C_4$)alkyl, halide, OH, or $OCF_3$;
$R_{11}$ is H, ($C_1$-$C_4$)alkyl, halide, OH, or $OCF_3$ and bond δ is a single bond;
$R_{12}$ is H, ($C_1$-$C_4$)alkyl, O($C_1$-$C_4$)alkyl, p-toluene sulfonyloxy or methane sulfonyloxy, halide, OH, $OCF_3$, or $R_{15}R_{16}$Si, where $R_{15}$ and $R_{16}$ are each independently ($C_1$-$C_4$)alkyl, furanyl or Ph, and bond δ is a single bond;
$R_{11}$ together with $R_{12}$ and the carbons to which each is attached to form an oxirane moiety form an ether group and bond δ is a single bond; or
$R_{11}$ and $R_{12}$ are absent and bond δ is a double bond; and wherein the composition is free of biological material of *illicium tashiroi*.

The subject application also provides for a composition comprising a compound having the structure of the formula (63)

wherein $R_{13}$ is C(O)OH, C(O)O($C_1$-$C_4$)alkyl, or C(O)S($C_1$-$C_4$) alkyl.

The subject application also provides for a compound having the structure of formula (73)

wherein, $R_{18}$ is H, ($C_1$-$C_4$)alkyl, or $CF_3$;
$R_{19}$ is H, O($C_1$-$C_4$)alkyl, ($C_1$-$C_4$)alkyl, halide, $OCF_3$, or $CF_3$;
$R_{20}$ is H, p-toluene sulfonyloxy, methane sulfonyloxy, C(O)($C_1$-$C_4$)alkyl, or OC(O)($C_1$-$C_4$)alkyl, and bond α is a single bond or $R_{20}$ is O and bond α is a double bond;
$R_{21}$, $R_{24}$, and $R_{25}$ are each independently H, O($C_1$-$C_4$) alkyl, ($C_1$-$C_4$)alkyl, halide, $OCF_3$, or $CF_3$;
$R_{22}$ is a halide, H, or ($C_1$-$C_4$)alkyl; and
$R_{23}$ is H, O($C_1$-$C_4$)alkyl, ($C_1$-$C_4$)alkyl, halide, $OCF_3$, $CF_3$ or Ph.

The subject application also provides for a process of producing a compound of the formula (72)

wherein,
$R_1$ is H, Bn, Bz, ($C_1$-$C_4$)alkyl, or $CF_3$;
$R_2$ is H, ($C_1$-$C_4$)alkyl, halide, OC(O)($C_1$-$C_4$)alkyl, OC(O) Ph, or $OCF_3$;
$R_3$ is p-toluene sulfonyloxy, methane sulfonyloxy, C(O) ($C_1$-$C_4$)alkyl, or OC(O)($C_1$-$C_4$)alkyl, bond α is a single bond and bond β is a double bond, or
$R_3$ is O, bond α is a double bond and bond β is a single bond;
$R_4$ is H, I, Br, Cl, Si($CH_3$)$_3$, ($C_1$-$C_4$)alkyl, or $OCF_3$;
$R_5$ is OH, OSi($CH_3$)$_3$, O($C_1$-$C_4$)alkyl, or $OCF_3$, and bond γ is a single bond, or
$R_5$ is O and bond γ is a double bond;

$R_6$ is H, $(C_1-C_4)$alkyl, or $CF_3$;

$R_7$ is H, OH, $(C_1-C_4)$alkyl, $CH_2OBn$, $CH_2O(C_1-C_4)$alkyl, $CH_2OH$, halide, $CH_2OCF_3$ or $OCF_3$ and bond ε is a single bond, or $R_7$ is $CH_2$ and bond ε is a double bond;

$R_8$, $R_9$, and $R_{10}$ are each independently H, $(C_1-C_4)$alkyl, halide, OH, or $OCF_3$; and $R_{11}$ and $R_{12}$ are each independently H, $(C_1-C_4)$alkyl, halide, OH, or $OCF_3$ and bond δ is a single bond, $R_{11}$ together with $R_{12}$ and the carbons to which each is attached to form an oxirane moiety form an ether group and bond δ is a single bond or $R_{11}$ and $R_{12}$ are absent and bond δ is a double bond, comprising subjecting a compound of the formula

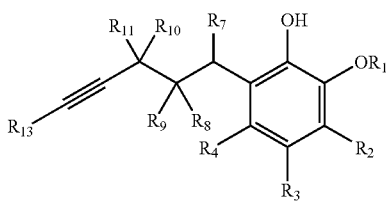
(71)

wherein $R_1$, $R_2$, $R_3$, $R_4$, $R_7$, $R_8$, $R_9$, $R_{10}$, and $R_{11}$ are defined as above; and $R_{13}$ is —C(O)OH, —C(O)O($C_1$-$C_4$)alkyl, or —C(O)S($C_1$-$C_4$)alkyl, to a tandem oxidative dearomatization-transannulation Diels-Alder reaction to obtain the compound.

The subject application also provides for a process of producing a compound of the formula

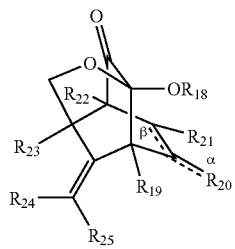
(73)

wherein, $R_{18}$ is H, $(C_1-C_4)$alkyl, or $CF_3$;

$R_{19}$ is H, $O(C_1-C_4)$alkyl, $(C_1-C_4)$alkyl, halide, $OCF_3$, or $CF_3$;

$R_{20}$ is H, p-toluene sulfonyloxy, methane sulfonyloxy, $C(O)(C_1-C_4)$alkyl, or $OC(O)(C_1-C_4)$alkyl, bond α is a single bond and bond β is a double bond or $R_{20}$ is O, bond α is a double bond and bond β is a single bond;

$R_{21}$, $R_{24}$, and $R_{25}$ are each independently H, $O(C_1-C_4)$alkyl, $(C_1-C_4)$alkyl, halide, $OCF_3$, or $CF_3$;

$R_{22}$ is a halide, H, or $(C_1-C_4)$alkyl; and $R_{23}$ is H, $O(C_1-C_4)$alkyl, $(C_1-C_4)$alkyl, halide, $OCF_3$, $CF_3$ or Ph comprising reacting a compound of the formula

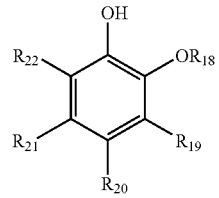
(74)

with a compound of the formula

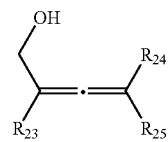
(75)

to obtain the compound.

The subject invention also provides a process of producing a compound of the formula

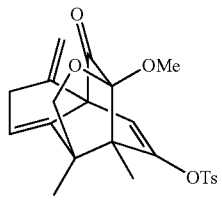

comprising
a) reacting the compounds of the formulae

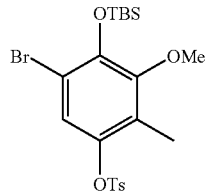 and 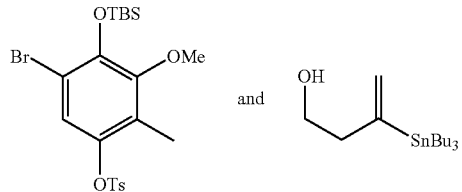

wherein $R_1$ are defined as above, with $Pd_2(dba)_3$, $^tBu_3P$, and DMF to obtain a compound of the formula

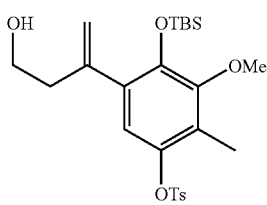

b) reacting the product of step a) with DMP and DCM to obtain a compound of the formula

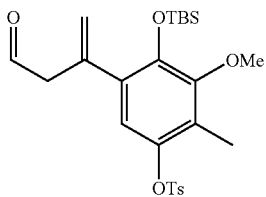

c) reacting the product of step b) with a compound of the formula

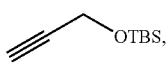

BuLi, and THF to obtain a compound of the formula

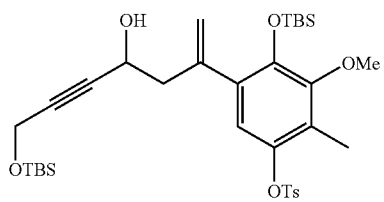

d) reacting the product of step c) first with MsCl and TEA and then with $Me_2Cu(CN)Li_2$ to obtain a compound of the formula

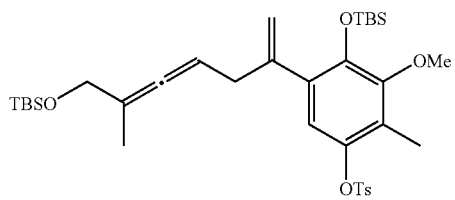

e) reacting the product of step d) with TBAF and THF to obtain a compound of the formula

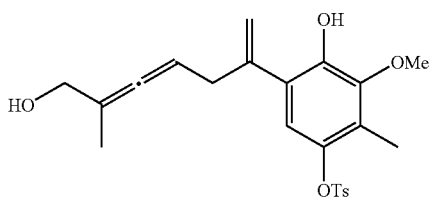

f) and reacting the product of step e) with PIDA and Toluene to thereby obtain the compound.

The subject invention further provides a process of producing a compound of the formula

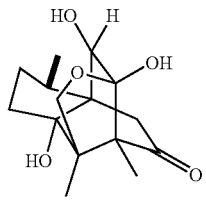

comprising a) reacting a compound of the formula

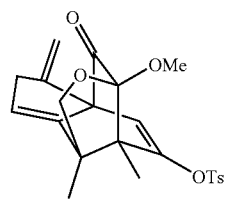

with $NaBH_4$ and MeOH to produce a compound of the formula

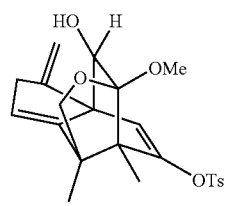

b) reacting the product of step a) with TMS-Imid to produce a compound of the formula

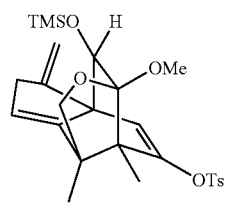

c) reacting the product of step b) with mCPBA and DCM to produce a compound of the formula

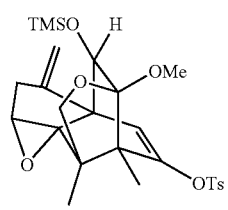

d) reacting the product of step c) with H₂, Pd/C 5%, and EtOAc to produce a compound of the formula

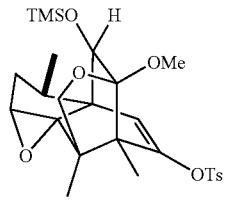

e) reacting the product of step d) with an acid in water to thereby obtain the compound.

DETAILED DESCRIPTION OF THE INVENTION

The subject application provides for a compound having the structure of the formula

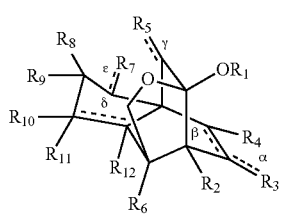

(72)

wherein, $R_1$ is H or Bz when no more than three of $R_8$, $R_9$, $R_{10}$ and $R_{11}$, are H, or $R_1$ is Bn, $(C_1-C_4)$ alkyl, or $CF_3$;

$R_2$ is H, $(C_1-C_4)$ alkyl, halide, $OC(O)(C_1-C_4)$alkyl, $OC(O)Ph$, or $OCF_3$;

$R_3$ is p-toluene sulfonyloxy, methane sulfonyloxy, $C(O)(C_1-C_4)$alkyl, or $OC(O)(C_1-C_4)$alkyl, bond α is a single bond, and bond β is a double bond or $R_3$ is O, bond α is a double bond and bond β is a single bond;

$R_4$ is H, I, Br, Cl, $Si(CH_3)_3$, $(C_1-C_4)$alkyl, or $OCF_3$;

$R_5$ is OH, $OSi(CH_3)_3$, $O(C_1-C_4)$ alkyl, or $OCF_3$, and bond γ is a single bond, or $R_5$ is O and bond γ is a double bond;

$R_6$ is H, $(C_1-C_4)$ alkyl, or $CF_3$;

$R_7$ is H, OH, $(C_1-C_4)$alkyl, $CH_2OBn$, $CH_2O(C_1-C_4)$alkyl, $CH_2OH$, halide, $CH_2OCF_3$ or $OCF_3$ and bond ε is a single bond, or $R_7$ is $CH_2$ and bond ε is a double bond;

$R_8$, $R_9$, and $R_{10}$ are each independently H, $(C_1-C_4)$alkyl, halide, OH, or $OCF_3$;

$R_{11}$ is H, $(C_1-C_4)$alkyl, halide, OH, or $OCF_3$ and bond δ is a single bond;

$R_{12}$ is H, $(C_1-C_4)$alkyl, $O(C_1-C_4)$alkyl, p-toluene sulfonyloxy or methane sulfonyloxy, halide, OH, $OCF_3$, or $R_{15}R_{16}Si$, where $R_{15}$ and $R_{16}$ are each independently $(C_1-C_4)$alkyl, furanyl or Ph, and bond δ is a single bond;

$R_{11}$ together with $R_{12}$ and the carbons to which each is attached to form an oxirane moiety form an ether group and bond δ is a single bond; or $R_{11}$ and $R_{12}$ are absent and bond δ is a double bond.

In one embodiment, the compound has the structure of the formula

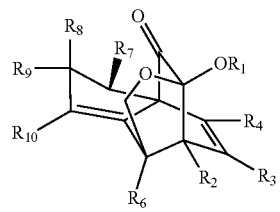

(64)

In an embodiment of the preceding formula, $R_1$, $R_4$, $R_8$, $R_9$, and $R_{10}$ are H, $R_2$, $R_6$, and $R_7$ are $CH_3$, and $R_3$ is p-toluene sulfonyloxy.

In another embodiment of the preceding formula, $R_1$, $R_8$, $R_9$, and $R_{10}$ are H, $R_2$, $R_6$, and $R_7$ are $CH_3$, $R_3$ is p-toluene sulfonyloxy and $R_4$ is I, Br, Cl, or $Si(CH_3)_3$.

In another embodiment, the compound has the structure of the formula

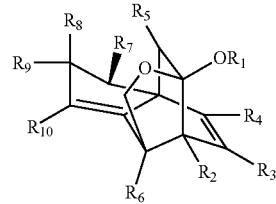

(65)

In an embodiment of the preceding formula, $R_1$, $R_4$, $R_8$, $R_9$, and $R_{10}$ are H, $R_2$, $R_6$ and $R_7$ are $CH_3$, $R_3$ is p-toluene sulfonyloxy, and $R_5$ is $OSi(CH_3)_3$.

In another embodiment of the preceding formula, $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

In another embodiment, the compound has the structure of the formula

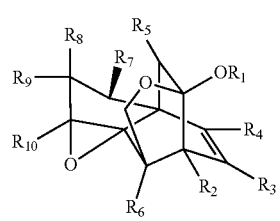

(66)

In an embodiment of the preceding formula, $R_1$, $R_4$, $R_8$, $R_9$, and $R_{10}$ are H, $R_2$, $R_6$ and $R_7$ are $CH_3$, $R_3$ is p-toluene sulfonyloxy and $R_5$ is $OSi(CH_3)_3$.

In another embodiment of the preceding formula, $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

In yet another embodiment, the compound has the structure of formula

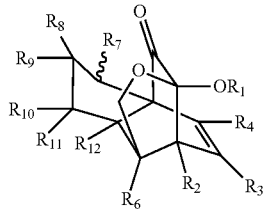
(68)

In an embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_8$, $R_9$, $R_{10}$, and $R_{11}$ are H, and $R_{12}$ is $R_{15}R_{16}Si$, wherein $R_{15}$ and $R_{16}$ are each independently $(C_1$-$C_4)$alkyl or Ph.

In another embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_8$, $R_9$, $R_{10}$, and $R_{11}$ are H, and $R_{12}$ is OH.

In another embodiment, the compound has the structure of formula

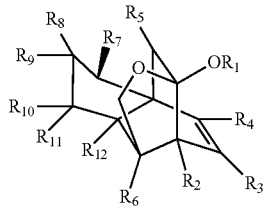
(69)

In an embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_5$ is $OSi(CH_3)_3$, $R_8$, $R_9$, $R_{10}$, and $R_{11}$ are H, and $R_{12}$ is OH.

The subject application also provides for a compound having the structure of the formula

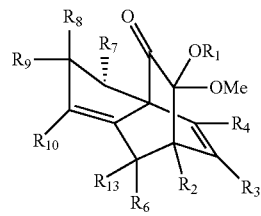
(63)

wherein $R_{13}$ is C(O)OH, C(O)O$(C_1$-$C_4)$alkyl, or C(O)S$(C_1$-$C_4)$alkyl.

In an embodiment of the preceding formula, $R_1$, $R_2$, $R_6$, and $R_7$ are $CH_3$, $R_3$ is p-toluene sulfonyloxy, $R_4$, $R_8$, $R_9$ and $R_{10}$ are H, and $R_{13}$ is C(O)SCH$_2$CH$_3$.

In another embodiment of the preceding formula, $R_1$, $R_2$, $R_6$, and $R_7$ are $CH_3$, $R_3$ is p-toluene sulfonyloxy, $R_4$ is I, BrCl, or $Si(CH_3)_3$, $R_8$, $R_9$ and $R_{10}$ are H, and $R_{13}$ is C(O)SCH$_2$CH$_3$.

In yet another embodiment of the preceding formula, $R_1$, $R_2$, $R_6$, and $R_7$ are $CH_3$, $R_3$ is p-toluene sulfonyloxy, $R_4$ is I, Br Cl, or $Si(CH_3)_3$, $R_8$, $R_9$ and $R_{10}$ are H, and $R_{13}$ is C(O)OH.

In another embodiment, a compound having the structure

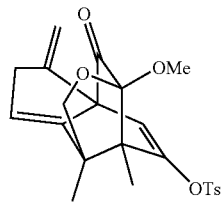

The subject application also provides for a composition comprising a compound having the structure of the formula

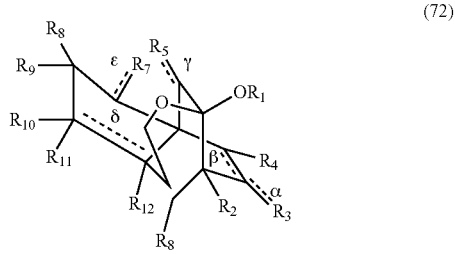
(72)

wherein, $R_1$ is H, Bn, Bz, $(C_1$-$C_4)$alkyl, or $CF_3$, $R_2$ is H, $(C_1$-$C_4)$ alkyl, halide, OC(O)$(C_1$-$C_4)$alkyl, OC(O)Ph, or $OCF_3$;

$R_3$ is p-toluene sulfonyloxy, methane sulfonyloxy, C(O)$(C_1$-$C_4)$alkyl, or OC(O)$(C_1$-$C_4)$alkyl, bond α is a single bond, and bond β is a double bond or $R_3$ is O, bond α is a double bond and bond β is a single bond;

$R_4$ is H, I, Br, Cl, $Si(CH_3)_3$, $(C_1$-$C_4)$alkyl, or $OCF_3$;

$R_5$ is OH, $OSi(CH_3)_3$, O$(C_1$-$C_4)$ alkyl, or $OCF_3$, and bond γ is a single bond, or $R_5$ is O and bond γ is a double bond;

$R_6$ is H, $(C_1$-$C_4)$ alkyl, or $CF_3$;

$R_7$ is H, OH, $(C_1$-$C_4)$alkyl, CH$_2$OBn, CH$_2$O$(C_1$-$C_4)$alkyl, CH$_2$OH, halide, CH$_2$OCF$_3$ or $OCF_3$ and bond ε is a single bond, or $R_7$ is CH$_2$ and bond ε is a double bond;

$R_8$, $R_9$, and $R_{10}$ are each independently H, $(C_1$-$C_4)$alkyl, halide, OH, or $OCF_3$;

$R_{11}$ is H, $(C_1$-$C_4)$alkyl, halide, OH, or $OCF_3$ and bond δ is a single bond;

$R_{12}$ is H, $(C_1$-$C_4)$alkyl, O$(C_1$-$C_4)$alkyl, p-toluene sulfonyloxy or methane sulfonyloxy, halide, OH, $OCF_3$, or $R_{15}R_{16}Si$, where $R_{15}$ and $R_{16}$ are each independently $(C_1$-$C_4)$alkyl, furanyl or Ph, and bond δ is a single bond;

$R_{11}$ together with $R_{12}$ and the carbons to which each is attached to form an oxirane moiety form an ether group and bond δ is a single bond; or $R_{11}$ and $R_{12}$ are absent and bond δ is a double bond; and wherein the composition is free of biological material of *illicium tashiroi*.

In an embodiment of the preceding formula, the compound has the structure of the formula

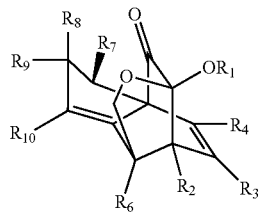
(64)

In an embodiment of the preceding formula, $R_1$, $R_4$, $R_8$, $R_9$, and $R_{10}$ are H, $R_2$, $R_6$, and $R_7$ are $CH_3$, and $R_3$ is p-toluene sulfonyloxy.

In another embodiment of the preceding formula, $R_1$, $R_8$, $R_9$, and $R_{10}$ are H, $R_2$, $R_6$, and $R_7$ are $CH_3$, $R_3$ is p-toluene sulfonyloxy and $R_4$ is I, Br, Cl, or $Si(CH_3)_3$.

In yet another embodiment, the compound has the structure of the formula

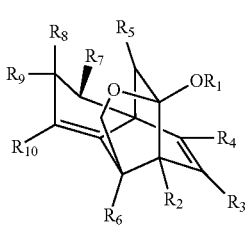
(65)

In an embodiment of the preceding formula, $R_1$, $R_4$, $R_8$, $R_9$, and $R_{10}$ are H, $R_2$, $R_6$ and $R_7$ are $CH_3$, $R_3$ is p-toluene sulfonyloxy, and $R_5$ is $OSi(CH_3)_3$.

In another embodiment of the preceding formula, $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

In yet another embodiment, the compound has the structure of the formula

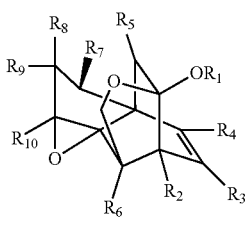
(66)

In an embodiment of the preceding formula, $R_1$, $R_4$, $R_8$, $R_9$, and $R_{10}$ are H, $R_2$, $R_6$ and $R_7$ are $CH_3$, $R_3$ is p-toluene sulfonyloxy and $R_5$ is $OSi(CH_3)_3$.

In another embodiment of the preceding formula, $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

In another embodiment, the compound has the structure of formula

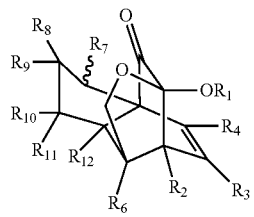
(68)

In an embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_8$, $R_9$, $R_{10}$, and $R_{11}$ are H, and $R_{12}$ is $R_{15}R_{16}Si$, wherein $R_{15}$ and $R_{16}$ are each independently $(C_1$-$C_4)$alkyl or Ph.

In another embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_8$, $R_9$, $R_{10}$, and $R_{11}$ are H, and $R_{12}$ is OH.

In another embodiment of the preceding formula, the compound has the structure of formula

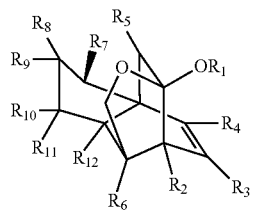
(69)

In an embodiment of the preceding formula, $R_1$, $R_2$, $R_6$, and $R_7$ are $CH_3$, $R_3$ is p-toluene sulfonyloxy, $R_4$ is I, Br, Cl, or $Si(CH_3)_3$, $R_5$ is $OSi(CH_3)_3$, $R_8$, $R_9$, $R_{10}$, and $R_{11}$ are H, and $R_{12}$ is OH.

The subject application also provides for a composition comprising a compound having the structure of the formula

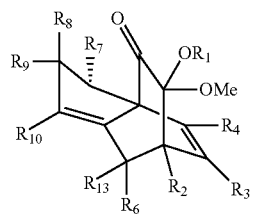
(63)

wherein $R_{13}$ is C(O)OH, $C(O)O(C_1$-$C_4)$alkyl, or $C(O)S(C_1$-$C_4)$ alkyl.

In another embodiment of the preceding formula, $R_1$, $R_2$, $R_6$, and $R_7$ are $CH_3$, $R_3$ is p-toluene sulfonyloxy, $R_4$, $R_8$, $R_9$ and $R_{10}$ are H, and $R_{13}$ is $C(O)SCH_2CH_3$.

In yet another embodiment of the preceding formula, $R_1$, $R_2$, $R_6$, and $R_7$ are $CH_3$, $R_3$ is p-toluene sulfonyloxy, $R_4$ is I, Br Cl, or $Si(CH_3)_3$, $R_8$, $R_9$ and $R_{10}$ are H, and $R_{13}$ is $C(O)SCH_2CH_3$.

In still another embodiment of the preceding formula, $R_1$, $R_2$, $R_6$, and $R_7$ are $CH_3$, $R_3$ is p-toluene sulfonyloxy, $R_4$ is I, Br Cl, or $Si(CH_3)_3$, $R_8$, $R_9$ and $R_{10}$ are H, and $R_{13}$ is C(O)OH.

The subject application also provides for a compound having the structure of formula

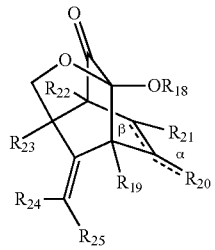
(73)

wherein, $R_{18}$ is H, $(C_1\text{-}C_4)$alkyl, or $CF_3$;
$R_{19}$ is H, $O(C_1\text{-}C_4)$alkyl, $(C_1\text{-}C_4)$alkyl, halide, $OCF_3$, or $CF_3$;
$R_{20}$ is H, p-toluene sulfonyloxy, methane sulfonyloxy, $C(O)(C_1\text{-}C_4)$alkyl, or $OC(O)(C_1\text{-}C_4)$alkyl, and bond α is a single bond or $R_{20}$ is O and bond α is a double bond;
$R_{21}$, $R_{24}$, and $R_{25}$ are each independently H, $O(C_1\text{-}C_4)$alkyl, $(C_1\text{-}C_4)$alkyl, halide, $OCF_3$, or $CF_3$;
$R_{22}$ is a halide, H, or $(C_1\text{-}C_4)$alkyl; and
$R_{23}$ is H, $O(C_1\text{-}C_4)$alkyl, $(C_1\text{-}C_4)$alkyl, halide, $OCF_3$, $CF_3$ or Ph.

In another embodiment of the preceding formula, $R_{18}$, $R_{19}$ and $R_{23}$ are $CH_3$, $R_{20}$ is p-toluene sulfonyloxy and bond α is a single bond, $R_{21}$, $R_{24}$ and $R_{25}$ are H, and $R_{22}$ is Br.

In yet another embodiment of the preceding formula, $R_{18}$, $R_{19}$ and $R_{23}$ are $CH_3$, $R_{20}$ is O and bond α is a double bond, $R_{21}$, $R_{24}$ and $R_{25}$ are H, and $R_{22}$ is Br.

In another embodiment, the compound has the structural formula

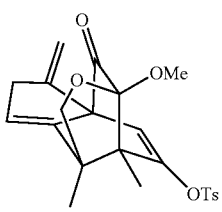

The subject application also provides for a process of producing a compound of the formula

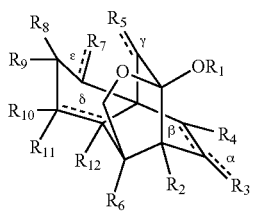
(72)

wherein,
$R_1$ is H, Bn, Bz, $(C_1\text{-}C_4)$alkyl, or $CF_3$;
$R_2$ is H, $(C_1\text{-}C_4)$alkyl, halide, $OC(O)(C_1\text{-}C_4)$alkyl, $OC(O)$Ph, or $OCF_3$;
$R_3$ is p-toluene sulfonyloxy, methane sulfonyloxy, $C(O)(C_1\text{-}C_4)$alkyl, or $OC(O)(C_1\text{-}C_4)$alkyl, bond α is a single bond and bond β is a double bond, or $R_3$ is O, bond α is a double bond and bond β is a single bond;
$R_4$ is H, I, Br, Cl, $Si(CH_3)_3$, $(C_1\text{-}C_4)$alkyl, or $OCF_3$;
$R_5$ is OH, $OSi(CH_3)_3$, $O(C_1\text{-}C_4)$alkyl, or $OCF_3$, and bond γ is a single bond, or
$R_5$ is O and bond γ is a double bond;
$R_6$ is H, $(C_1\text{-}C_4)$alkyl, or $CF_3$;
$R_7$ is H, OH, $(C_1\text{-}C_4)$alkyl, $CH_2OBn$, $CH_2O(C_1\text{-}C_4)$alkyl, $CH_2OH$, halide, $CH_2OCF_3$ or $OCF_3$ and bond ε is a single bond, or
$R_7$ is $CH_2$ and bond ε is a double bond;
$R_8$, $R_9$, and $R_{10}$ are each independently H, $(C_1\text{-}C_4)$alkyl, halide, OH, or $OCF_3$; and
$R_{11}$ and $R_{12}$ are each independently H, $(C_1\text{-}C_4)$alkyl, halide, OH, or $OCF_3$ and bond δ is a single bond,
$R_{11}$ together with $R_{12}$ and the carbons to which each is attached to form an oxirane moiety form an ether group and bond δ is a single bond or
$R_{11}$ and $R_{12}$ are absent and bond δ is a double bond,
comprising subjecting a compound of the formula

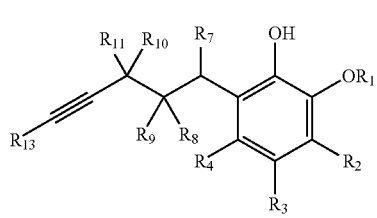
(71)

wherein $R_1$, $R_2$, $R_3$, $R_4$, $R_7$, $R_8$, $R_9$, $R_{10}$, and $R_{11}$ are defined as above; and
$R_{13}$ is —C(O)OH, —C(O)O$(C_1\text{-}C_4)$alkyl, or —C(O)S$(C_1\text{-}C_4)$alkyl,
to a tandem oxidative dearomatization-transannulation Diels-Alder reaction to obtain the compound.

In an embodiment of the preceding process, the tandem oxidative dearomatization-transannulation Diels-Alder reaction comprises reacting a compound of the formula

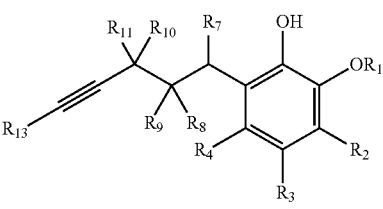
(71)

with phenyliodine(III)diacetate (PIDA) to obtain a compound of the formula

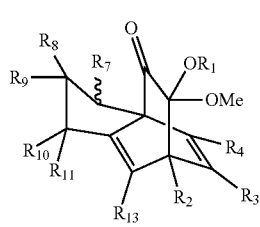
(70)

In an embodiment of the preceding process, further comprising subjecting the compound of the formula

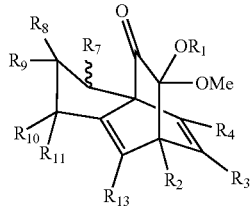

(70)

to a ring closure reaction to obtain the compound of the formula

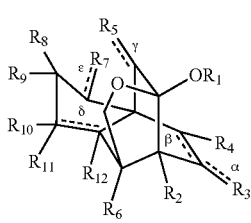

(72)

In an embodiment of the preceding process, the ring closure reaction comprises hydrochloric acid.

In an embodiment of the process of the subject invention, the process further comprising
a) reducing the compound of the formula

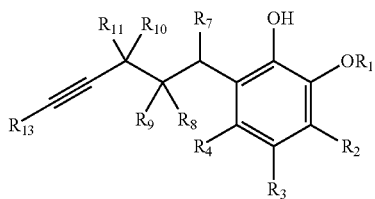

(71)

to obtain a compound of the formula

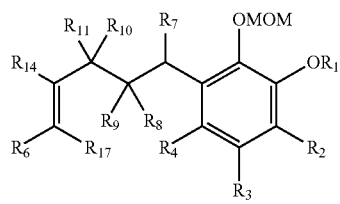

(62)

wherein
MOM is $CH_2OCH_3$;
$R_{14}$ is H, $O(C_1-C_4)$alkyl, $(C_1-C_4)$alkyl, or $R_{15}R_{16}Si$, wherein $R_{15}$ and $R_{16}$ are each independently $(C_1-C_4)$alkyl, furanyl or Ph;
and
$R_{17}$ is —$C(O)O(C_1-C_4)$alkyl, —$C(O)OH$, or —$CH_2OH$.

In another embodiment of the subject invention, the process further comprises the steps of:
a) reacting a compound of the formula

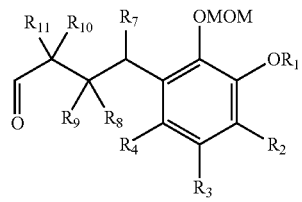

(12)

wherein MOM is $CH_2OCH_3$,
with Bestmann reagent, and $K_2CO_3$ to obtain a compound of the formula

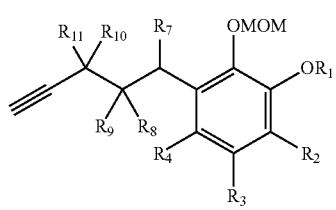

(24)

b) reacting the product of step a) sequentially with
i) n-butyl lithium and $CO_2$,
ii) 1-[3-(dimethylamino)propyl]-3-ethylcarbiimide hydrochloroide (EDCI), $(C_1-C_4)$alkyl mercaptan or $(C_1-C_4)$alkyl alcohol, dimethylaminopyridine (DMAP), and 4-(dicyanomethene)-2-methyl-6-(4-dimethylaminostyryl)-4H-pyran (DCM), and
iii) hydrochloric acid
to obtain a compound of the formula

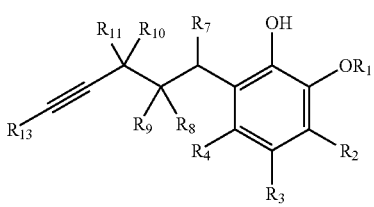

(71)

In an embodiment of the of the subject invention, further comprising the compound of the formula

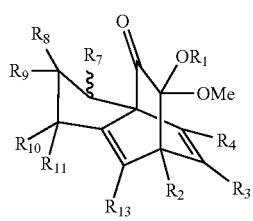

(70)

a) reacting with lithium diisoproplyamine (LDA) and methyl iodide to obtain a compound of the formula

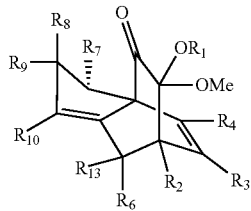
(31)

b) reacting the product step a) sequentially with
   i) H$_2$, Pd/C,
   ii) 1,1,1-Triacetoxy-1,1-dihydro-1,2-benziodoxol-3(1H)-one (Dess-Martin reagent),
   iii) lithium diisoproplyamine and H+, and
   iv) NH$_2$NH$_2$ and NaOH
to obtain a compound of the formula

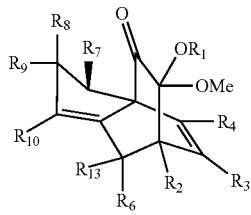
(32)

c) reacting the product of step b) with
   i) (CH$_3$CH$_2$)$_3$SiH and Pd/C, and
   ii) 9-borabicyclo[3.3.1]nonane-pyridine(9-BBN-pyr) or diisobutylaluminum hydride (DIBAL-H)
to obtain a compound of the formula

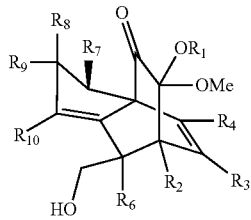
(33)

d) reacting the product of step c) with aqueous hydrochloric acid to obtain a compound of the formula

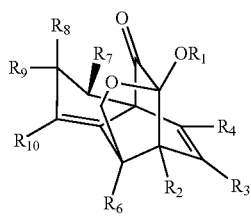
(34)

e) reacting the product of step d) with a suitable source of hydride ion then a trimethylsilane (TMS) halide to obtain a compound of the formula

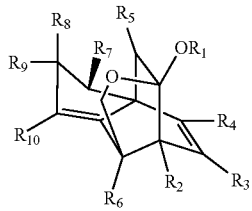
(35)

f) reacting the product of claim e) with m-chloroperoxybenzoic acid (mCPBA) to obtain a compound of the formula

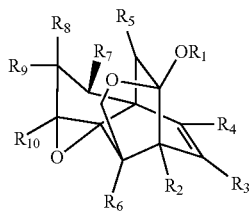
(36)

and g) reacting the product of step f) with a suitable source of hydride ion and a suitable source of hydroxide ion,
to thereby obtain the compound.

In another embodiment of the of the subject invention, further comprising the compound of the formula

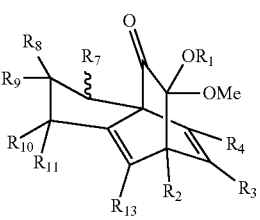
(70)

a) reacting with lithium diisoproplyamine (LDA) and methyl iodide to obtain a compound of the formula

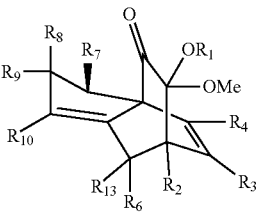
(31)

b) reacting the product step a) with BH₃ in tetrahydrofuran (THF)
to obtain a compound of the formula

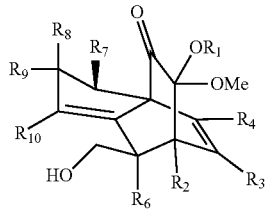
(33)

c) reacting the product of step b) with hydrochloric acid to obtain a compound with the formula

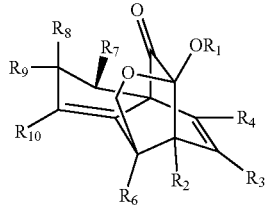
(34)

d) reacting the product of step c) with
   i) a suitable source of hydride ion, and
   ii) trimethylsilyl chloride (TMSCl)
   to obtain a compound of the formula

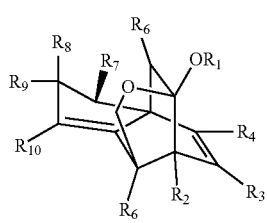
(35)

e) reacting the product of claim d) with m-chloroperoxybenzoic acid (mCPBA) to obtain a compound of the formula

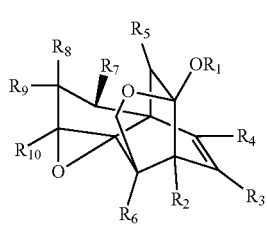
(36)

and f) reacting the product of step e) with a suitable source of hydride ion and a suitable source of hydroxide ion, to thereby obtain the compound.

In yet another embodiment of the of the subject invention, further comprising the compound of the formula

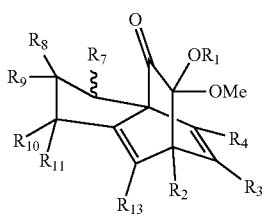
(70)

a) reacting with lithium diisoproplyamine (LDA) and methyl iodide to obtain a compound of the formula

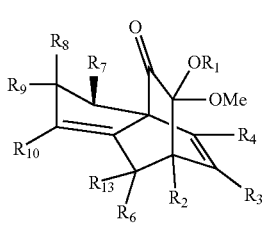
(31)

b) reacting the product step a) with
   i) (CH₃CH₂)₃SiH, Pd/C 10% and
   ii) a suitable source of hydride ion
   to obtain a compound of the formula

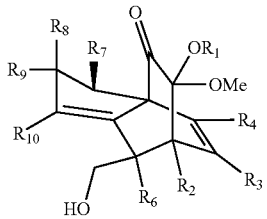
(33)

c) reacting the product of step b) with aqueous hydrochloric acid to obtain a compound of the formula

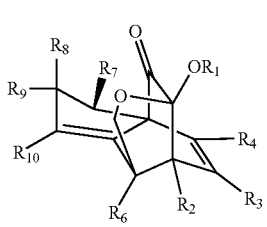
(34)

d) reacting the product of step c) with hydride ion and trimethylsilyl chloride (TMSCl) to obtain a compound of the formula (35)

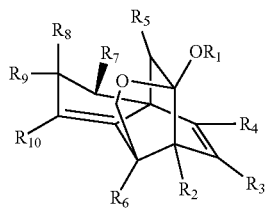

e) reacting the product of claim d) with m-chloroperoxybenzoic acid (MCPBA) to obtain a compound of the formula (36)

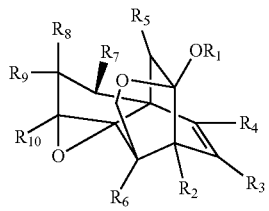

and f) reacting the product of step e) with a suitable source of hydride ion and a suitable source of hydroxide ion, to thereby obtain the compound.

In an embodiment of the of the subject invention, further comprising the compound of the formula (62)

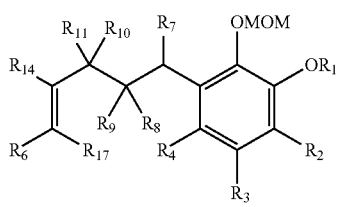

a) reacting with a suitable source of hydride ion and hydrochloric acid to obtain a compound of the formula (38)

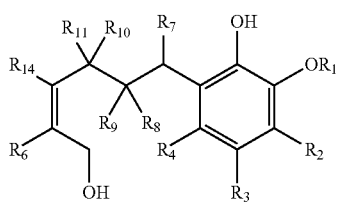

b) reacting the product of step a) with phenyliodine (III) diacetate (PIDA) according to a tandem oxidative dearomatization-transannular Diels-Alder reaction to obtain a compound of the formula (39)

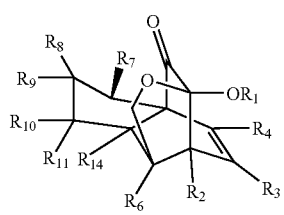

c) reacting the product of step b) with hydrogen peroxide, $(C_1-C_4)$alkyl peroxide or benzyl peroxide and NaOH to obtain a compound of the formula (40)

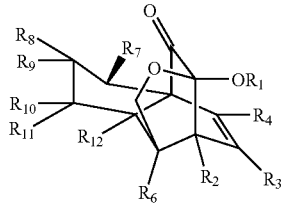

d) reacting the product of step c) with a suitable source of hydride ion to obtain a compound of the formula (41)

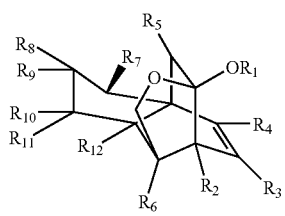

e) reacting the product of step d) with a suitable source of hydroxide ion to thereby obtain the compound.

In an embodiment, the subject application provides for a process to produce the compound having the formula

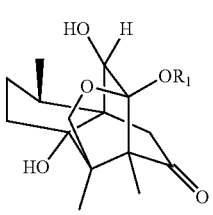

wherein R₁ is H or OBz,
comprising:
a) reacting a compound with the formula

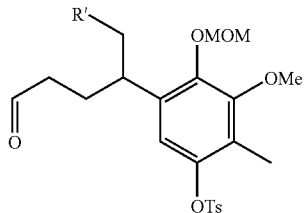

wherein R' is H or OBn;
MOM is CH₂OCH₃;
Me is CH₃; and
Ts is p-toluene sulfonyl,
with Bestmann reagent, and K₂CO₃ to obtain a compound of the formula

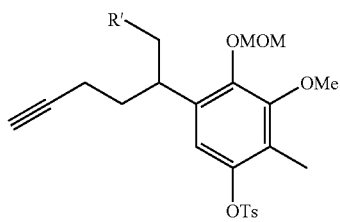

b) reacting the product of step a) sequentially with
  i) n-butyl lithium and CO₂,
  ii) 1-[3-(dimethylamino)propyl]-3-ethylcarbiimide hydrochloroide (EDCI), (C₁-C₄)alkyl mercaptan or (C₁-C₄)alkyl alcohol, dimethylaminopyridine (DMAP), and 4-(dicyanomethene)-2-methyl-6-(4-dimethylaminostyryl)-4H-pyran (DCM), and
  iii) hydrochloric acid
to obtain a compound of the formula

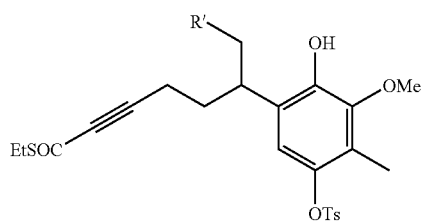

wherein EtSOC is —CH₃CH₂S(O)C;

c) subjecting the product of step b) to the tandem oxidative dearomatization-transannular Diels-Alder reaction using phenyliodine (III)diacetate (PIDA) to obtain a compound of the formula

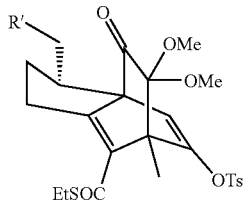

d) reacting the product of step c) with lithium diisoproplyamine (LDA) and methyl iodide to obtain a compound of the formula

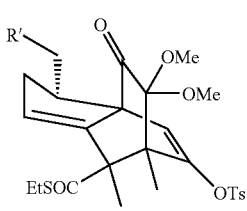

e) reacting the product of step d) sequentially with
  i) H₂, Pd/C,
  ii) 1,1,1-Triacetoxy-1,1-dihydro-1,2-benziodoxol-3 (1H)-one (Dess-Martin reagent),
  iii) lithium diisoproplyamine (LDA) and H⁺, and
  iv) NH₂NH₂ and NaOH
to obtain a compound of the formula

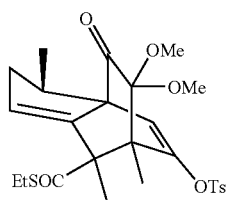

f) reacting the product of step e) with
  i) (CH₃CH₂)₃SiH and Pd/C, and
  ii) 9-borabicyclo[3.3.1]nonane-pyridine(9-BBN-pyr) or diisobutylaluminum hydride (DIBAL-H)
to obtain a compound of the formula

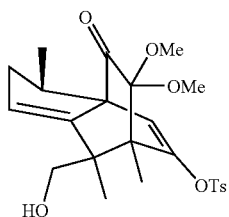

g) reacting the product of step f) with aqueous hydrochloric acid to obtain a compound of the formula

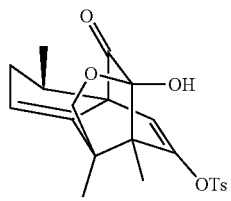

h) reacting the product of step g) with a suitable source of hydride ion then a trimethylsilane (TMS) halide to obtain a compound of the formula

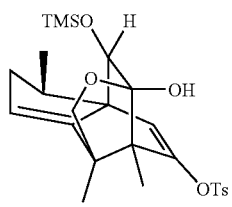

wherein TMSO is OSi(CH$_3$)$_3$;

i) reacting the product of step h) with m-chloroperoxybenzoic acid (MCPBA) to obtain a compound of the formula

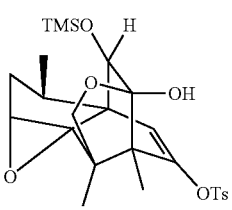

j) reacting the product of step i) with a suitable source of hydride ion and a suitable source of hydroxide ion to thereby obtain the compound.

In another embodiment, the subject application provides for a process to produce the compound having the formula

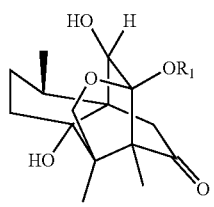

wherein R$_1$ is H or OBz, comprising:

a) reacting a compound with the formula

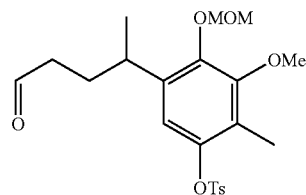

wherein MOM is CH$_2$OCH$_3$;

Me is CH$_3$; and

Ts is p-toluene sulfonyl, with Bestmann reagent, and K$_2$CO$_3$ to obtain a compound of formula

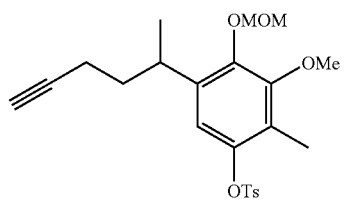

b) reacting the product of step a) sequentially with
i) n-butyl lithium and CO$_2$,
ii) n-iodosuccinamide (NIS) or n-bromosuccinamide (NBS) or n-chlorosuccinamide (NCS) or trimethylsilyl-trimethylsilyl (TMS-TMS), and Pd and
iii) hydrochloric acid
to obtain a compound of the formula

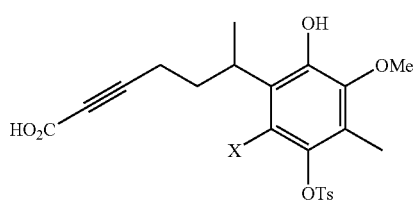

wherein X is I, Br, Cl, or Si(CH$_3$)$_3$;

c) subjecting the product of step b) to the tandem oxidative dearomatization-transannular Diels-Alder reaction using phenyliodine (III)diacetate (PIDA) to obtain a compound of the formula

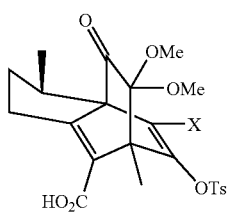

d) reacting the product of step c) with lithium diisopropylamine (LDA) and methyl iodide to obtain a compound of the formula

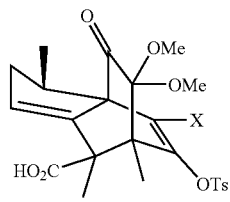

e) reacting the product of step d) with $BH_3$ in tetrahydrofuran (THF)
to obtain a compound of the formula

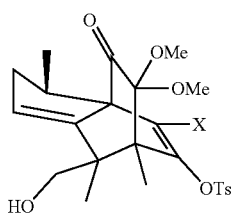

f) reacting the product of step e) with hydrochloric acid to obtain a compound with the formula

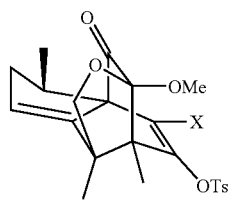

g) reacting the product of step f) with
  i) a suitable source of hydride ion, and
  ii) trimethylsilyl chloride (TMSCl)
to obtain a compound of the formula

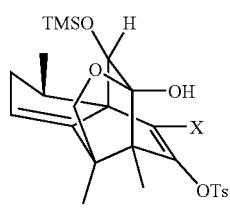

wherein TMSO is $OSi(CH_3)_3$;

h) reacting the product of step g) with m-chloroperoxybenzoic acid (mCPBA) to obtain a compound of the formula

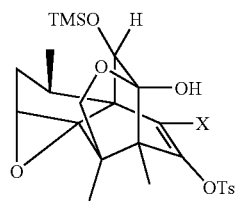

i) reacting the product of step h) with a suitable source of hydride ion and a suitable source of hydroxide ion
to thereby obtain the compound.

In an embodiment, the subject application provides for a process to produce the compound having the formula

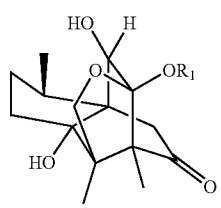

wherein $R_1$ is H or OBz,
comprising:
a) reacting a compound with the formula

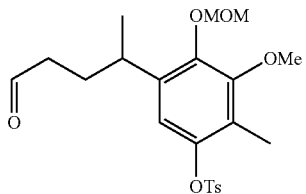

wherein MOM is $CH_2OCH_3$;
Me is $CH_3$; and
Ts is p-toluene sulfonyl,
with Bestmann reagent, and $K_2CO_3$ to obtain a compound of formula

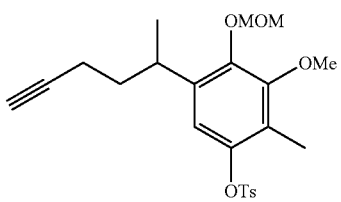

b) reacting the product of step a) sequentially with
  i) n-butyl lithium and $CO_2$,
  ii) 1-[3-(dimethylamino)propyl]-3-ethylcarbiimide hydrochloroide (EDCI), ($C_1$-$C_4$)alkyl mercaptan or ($C_1$-$C_4$)alkyl alcohol, dimethylaminopyridine (DMAP), and 4-(dicyanomethene)-2-methyl-6-(4-dimethylaminostyryl)-4H-pyran (DCM), iii) n-iodosuccinamide (NIS) or n-bromosuccinamide (NBS) or n-chlorosuccinamide (NCS) or trimethylsilyl-trimethylsilyl (TMS-TMS), and Pd and iv) hydrochloric acid to obtain a compound of the formula

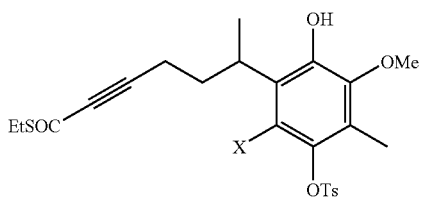

wherein EtSOC is —CH$_3$CH$_2$S(O)C; and

X is I, Br, Cl, or Si(CH$_3$)$_3$;

c) subjecting the product of step b) to the tandem oxidative dearomatization-transannular Diels-Alder reaction using phenyliodine (III)diacetate (PIDA) to obtain a compound of the formula

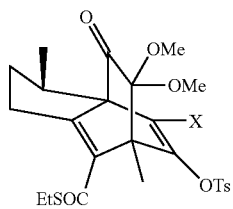

d) reacting the product of step c) with lithium diisoproplyamine (LDA) and methyl iodide to obtain a compound of the formula

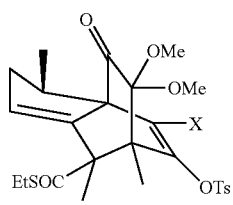

e) reacting the product of step d) with i) (CH$_3$CH$_2$)$_3$SiH and Pd/C; and ii) a suitable source of hydride ion to obtain a compound of the formula

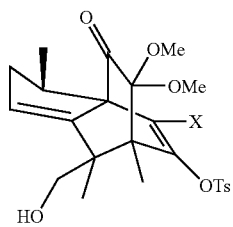

f) reacting the product of step e) with aqueous hydrochloric acid to obtain a compound of the formula

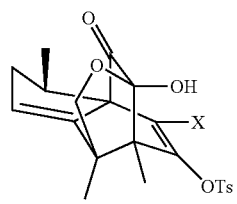

g) reacting the product of step f) with hydride ion and trimethylsilyl chloride (TMSCl) to obtain a compound of the formula

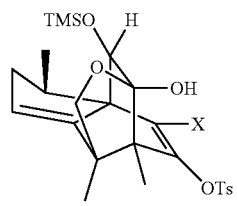

h) reacting the product of step g) with m-chloroperoxybenzoic acid (mCPBA) to obtain a compound of the formula

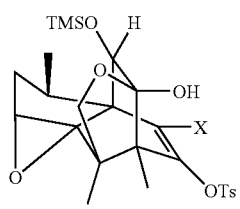

wherein TMSO is OSi(CH$_3$)$_3$;

i) reacting the product of step h) with i) a suitable source of hydride ion and a suitable source of hydroxide ion and ii) Zn or (PhSe)$_2$ or NaI, to thereby obtain the compound.

In yet another embodiment, the subject application provides for a process to produce the compound having the formula

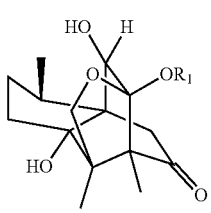

wherein $R_1$ is H or OBz, comprising:

a) reacting a compound with the formula

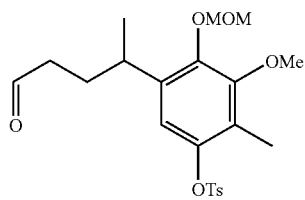

wherein MOM is $CH_2OCH_3$;

Me is $CH_3$; and

Ts is p-toluene sulfonyl, with Bestmann reagent, and $K_2CO_3$ to obtain a compound of the formula

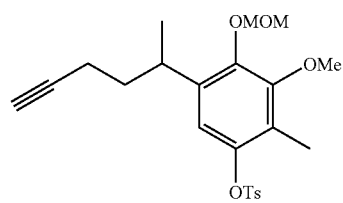

b) reacting the product of step a) sequentially with
   i) n-butyl lithium and $CO_2$,
   ii) 1-[3-(dimethylamino)propyl]-3-ethylcarbiimide hydrochloroide (EDCI), $(C_1$-$C_4)$alkyl mercaptan or $(C_1$-$C_4)$alkyl alcohol, dimethylaminopyridine (DMAP), and 4-(dicyanomethene)-2-methyl-6-(4-dimethylaminostyryl)-4H-pyran (DCM),
   iii) n-iodosuccinamide (NIS) or n-bromosuccinamide (NBS) or n-chlorosuccinamide (NCS) or trimethylsilyl-trimethylsilyl (TMS-TMS), and Pd and
   iv) hydrochloric acid to obtain a compound of the formula

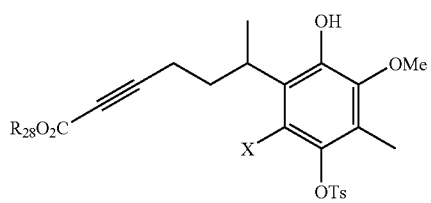

wherein $R_{28}$ is $(C_1$-$C_4)$alkyl; and

X is I, Br, Cl, or $Si(CH_3)_3$;

c) reacting the product of step b) with
   i) $R_{16}R_{15}SiCuLi$ and $I_2$ and
   ii) $Me_4Sn$ and Pd, to obtain a compound of the formula

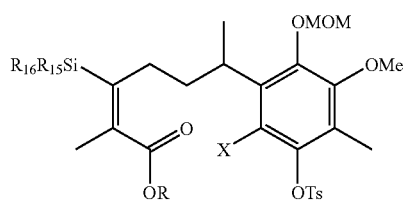

wherein R is $(C_1$-$C_4)$alkyl; and $R_{15}$ and $R_{16}$ are each independently $(C_1$-$C_4)$alkyl, furanyl or Ph;

d) reacting the product of step c) with a suitable source of hydride ion and hydrochloric acid to obtain a compound of the formula

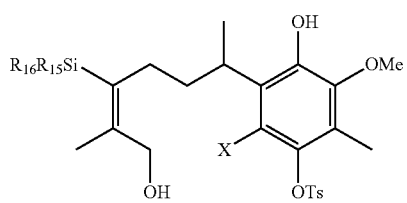

e) subjecting the product of step d) to the tandem oxidative dearomatization-transannular Diels-Alder reaction using phenyliodine (III)diacetate (PIDA) to obtain a compound of the formula

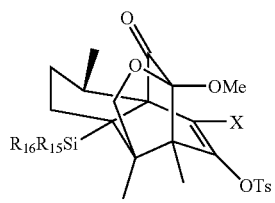

f) reacting the product of step e) with hydrogen peroxide, $(C_1$-$C_4)$alkyl peroxide or benzyl peroxide and NaOH to obtain a compound of the formula

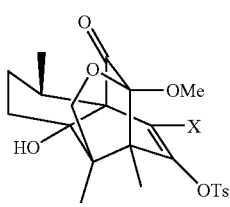

g) reacting the product of step f) a suitable source of hydride ion to obtain a compound of the formula

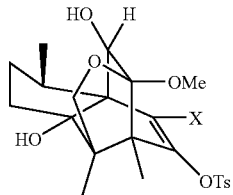

h) reacting the product of step g) with a suitable source of hydroxide ion and HCl to thereby obtain the compound.

The subject application also provides for a process of producing a compound of the formula

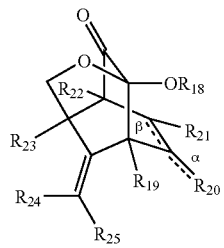
(73)

wherein, $R_{18}$ is H, $(C_1-C_4)$alkyl, or $CF_3$;

$R_{19}$ is H, $O(C_1-C_4)$alkyl, $(C_1-C_4)$alkyl, halide, $OCF_3$, or $CF_3$;

$R_{20}$ is H, p-toluene sulfonyloxy, methane sulfonyloxy, $C(O)(C_1-C_4)$alkyl, or $OC(O)(C_1-C_4)$alkyl, bond α is a single bond and bond β is a double bond or $R_{20}$ is O, bond α is a double bond and bond β is a single bond;

$R_{21}$, $R_{24}$, and $R_{25}$ are each independently H, $O(C_1-C_4)$alkyl, $(C_1-C_4)$alkyl, halide, $OCF_3$, or $CF_3$;

$R_{22}$ is a halide, H, or $(C_1-C_4)$alkyl; and $R_{23}$ is H, $O(C_1-C_4)$alkyl, $(C_1-C_4)$alkyl, halide, $OCF_3$, $CF_3$ or Ph comprising reacting a compound of the formula

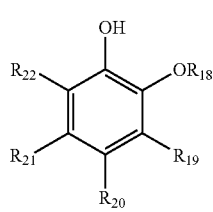
(74)

with a compound of the formula

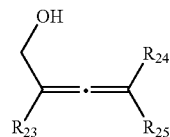
(75)

to obtain the compound.

The subject application also provides for a compound produced by any one of the preceding processes.

The subject application also provides for a pharmaceutical composition comprising any one of the preceding compounds or compositions and a pharmaceutically acceptable carrier.

The subject invention also provides a process of producing a compound of the formula

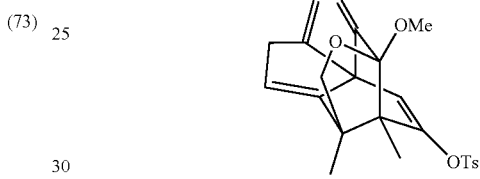

comprising
a) reacting the compounds of the formulae

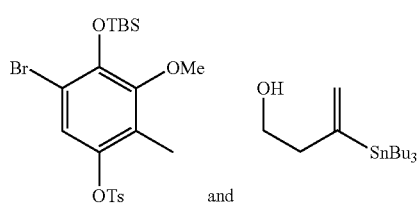

wherein $R_1$ are defined as above, with $Pd_2(dba)_3$, $^tBu_3P$, and DMF to obtain a compound of the formula

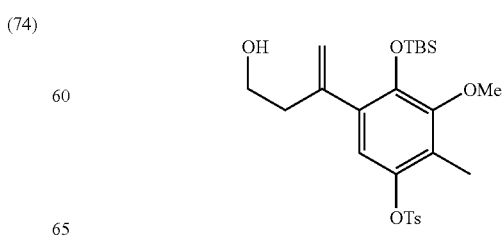

b) reacting the product of step a) with DMP and DCM to obtain a compound of the formula

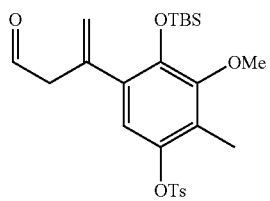

c) reacting the product of step b) with a compound of the formula

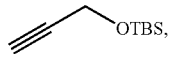

BuLi, and THF to obtain a compound of the formula

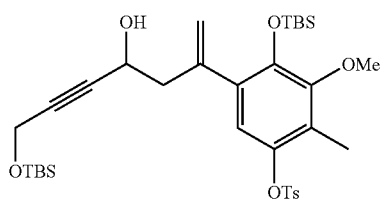

d) reacting the product of step c) first with MsCl and TEA and then with $Me_2Cu(CN)Li_2$ to obtain a compound of the formula

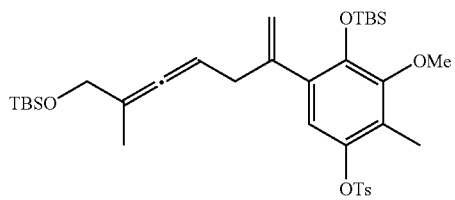

e) reacting the product of step d) with TBAF and THF to obtain a compound of the formula

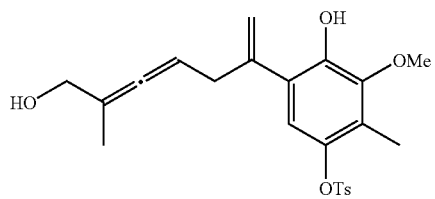

f) and reacting the product of step e) with PIDA and Toluene to thereby obtain the compound.

The subject invention further provides a process of producing a compound of the formula

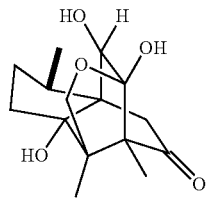

comprising
b) reacting a compound of the formula

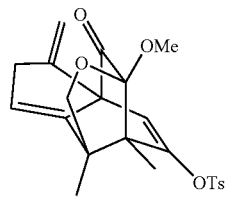

with $NaBH_4$ and MeOH to produce a compound of the formula

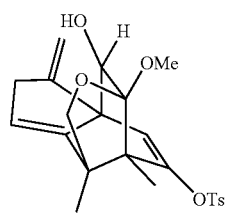

b) reacting the product of step a) with TMS-Imid to produce a compound of the formula

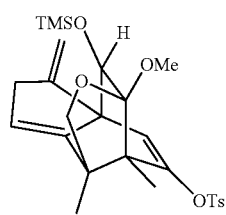

c) reacting the product of step b) with mCPBA and DCM to produce a compound of the formula

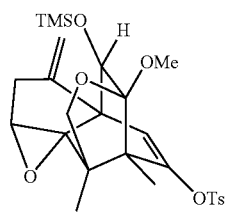

d) reacting the product of step c) with H$_2$, Pd/C 5%, and EtOAc to produce a compound of the formula

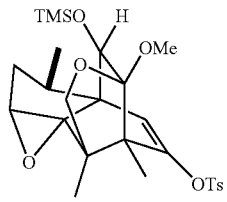

e) reacting the product of step d) with an acid in water to thereby obtain the compound.

Throughout this application the abbreviation "Bz" is used to refer to benzene and the abbreviation "Bn" is used to refer to benzyl.

Discussion

The subject invention provides a free-standing synthetic route as an alternative to the complexities of obtaining either 1 or 2 from natural sources. The synthetic route also provides a diverted total synthesis to explore tashironin analogs.

One approach to constructing the structural backbone of debenzoyltashironin employed a tandem oxidative dearomatization-transannular Diels-Alder reaction to rapidly generate the highly substituted tetracyclic core 5 from a relatively simple precursor 4 (Scheme 1). According to our design, the key substrate 4 is prepared from a suitably protected aromatic precursor 3.

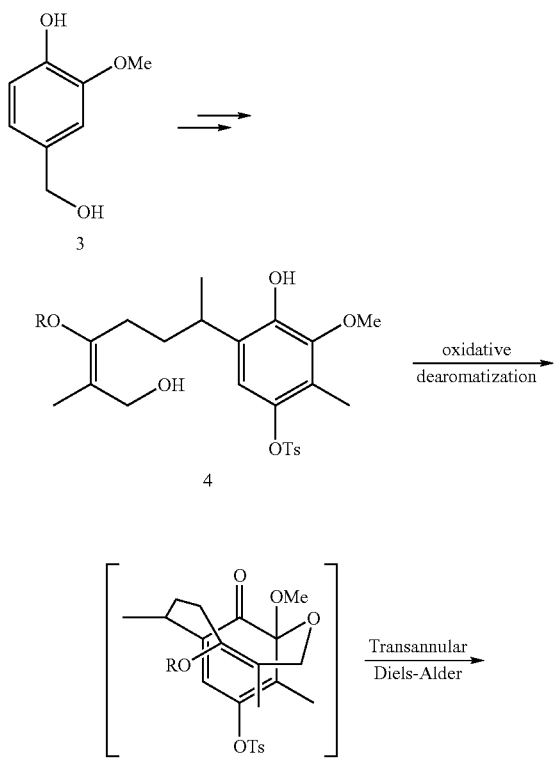

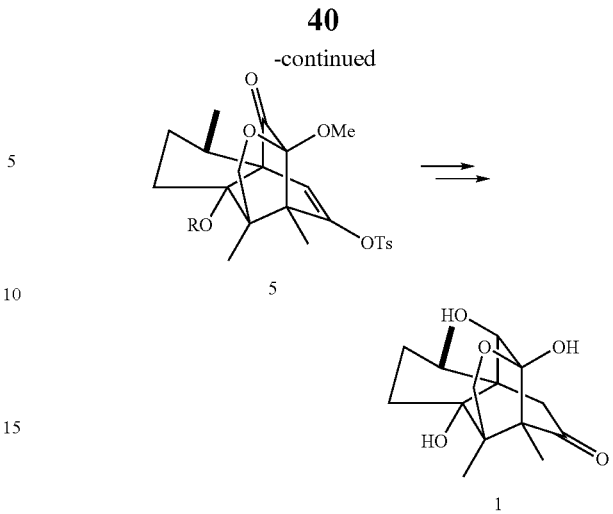

We noted that under suitable reaction conditions, 4 can undergo intramolecular oxidative dearomatization, following the protocol of Pelter and Tamura (Pelter, et al., *Tetrahedron Lett.* 1988, 29, 677; Tamura, et al., *Org. Chem.* 1987, 52, 3927; Magdziak, et al., *Chem. Rev.* 2004, 104, 1383.) to give rise to an intermediate cyclized species that can be configured to undergo a transannular Diels-Alder reaction to afford 5 which in turn can be progressed to 1. Success of this strategy is predicated on the ability of the methyl stereocenter in the tandem precursor 4 to exert diastereofacial control in the oxidative dearomatization step.

EXPERIMENTAL DETAILS

Example 1

Formation of the Tetracyclic Core

Our synthesis commenced with commercially available vanillyl alcohol 3a. Compound 3a was treated with catalytic amounts of tosyl acid in methanol to afford 3b, presumably via a p-quinone methide intermediate (Scheme 2). The aromatic methyl group was then installed regiospecifically at the more hindered site through directed lithiation followed by methylation to afford 6. A subsequent 2,3-Dichloro-5,6-dicyano-1,4-benzoquinone (DDQ)-mediated oxidation gave rise to 2-methylvanillin 7 in 44% overall yield from 3a. Crotylation of the phenolic hydroxyl group, followed by a Claisen rearrangement produced phenol 8. For greater flexibility in later transformations, the phenol was protected either as a benzyl ether 9a or as a MOM ether 9b. Baeyer-Villiger oxidation of these compounds followed by hydrolysis afforded phenols 10a and 10b in 54% and 95% overall yields, respectively, from 8. The resultant phenolic hydroxyl group in each compound was then tosylated to produce 11a and 11b in the yields shown. These compounds were hydroformylated with acetyl acetonate dicarbonyl rhodium (1) (Rh(CO)$_2$(acac)) and the Billig bis-organophosphite ligand according to Buchwald's protocol, to give exclusively the desired linear aldehydes 12a and 12b in 90% and 82% yields, respectively (Cuny, et al., *J. Am. Chem. Soc.* 1993, 115, 2066).

Scheme 2. Synthesis of Aldehydes 12a and 12b[a]

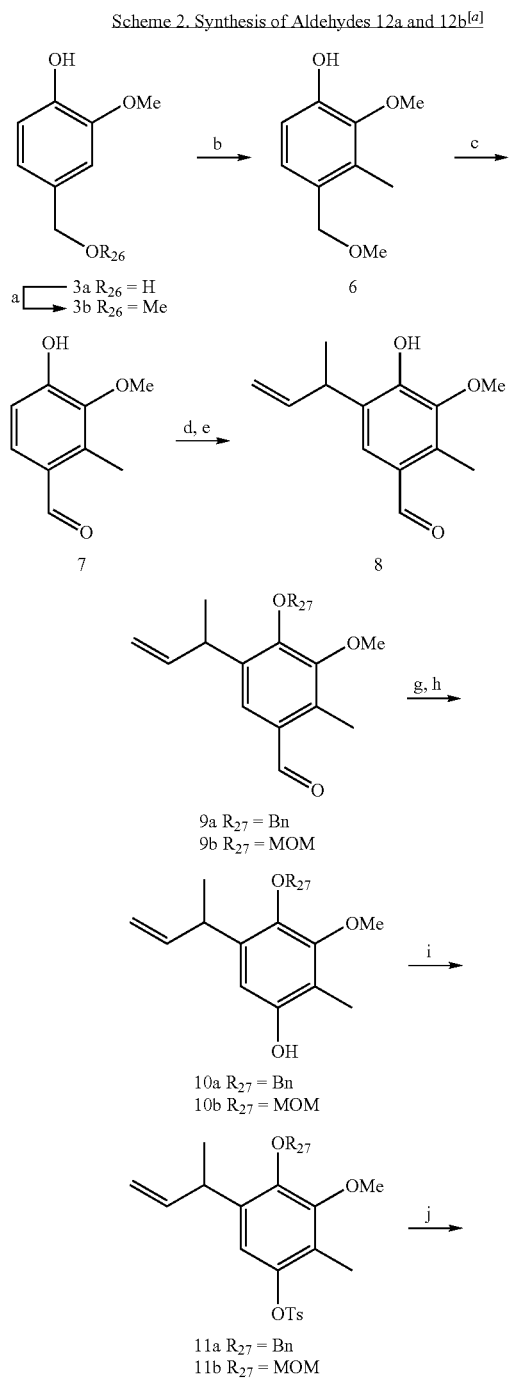

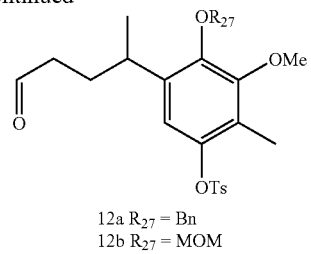

12a R$_{27}$ = Bn
12b R$_{27}$ = MOM

[a] Key: a) MeOH, p-TSA, rt, 100%; b) BuLi, THF, -15° C. to 0° C., then -10° C., MeI; c) DDQ, CH$_2$Cl$_2$/H$_2$O 19:1, rt, 44% for two steps; d) Crotyl bromide, K$_2$CO$_3$, acetone, reflux; e) neat, 185° C., 81% for two steps; f) MOMCl, DIEA, CH$_2$Cl$_2$, rt, 98% or BnBr, K$_2$CO$_3$, acetone, reflux, 93%; g) m-CPBA, CH$_2$Cl$_2$, 0° C.; h) Et$_3$N, CH$_2$Cl$_2$/MeOH 1:1, rt, 61% (10a) and 96% (10b) over two steps; i) TsCl, Et$_3$N, CH$_2$Cl$_2$, rt, 88% (11a) and 91% (11b); j) Rh(CO)$_2$(acac), Billig Ligand, CO/H$_2$ 1:1, toluene, 60° C., 90% (12a) and 82% (12b).

At this juncture, we tested the feasibility of our key transformation. Toward this end, subjection of aldehyde 12a to Roskamp conditions followed by methylation of the resulting β-ketoester gave rise to 13 (Scheme 3) (Holmquist, et al., *J. Org. Chem.* 1989, 54, 3258). Treatment of 13 with methanesulfonyl chloride and triethylamine (TEA) in methylene chloride led to the formation of the desired (E)-tetrasubstituted olefin 14 in modest yield. Olefin geometry was determined by Nuclear Overhauser Effect (NOE) studies of the reduced product. Finally, reduction of the ethyl ester with diisobutylaluminium hydride (DIBAL-H), followed by benzyl deprotection gave the key substrate, 15.

In the event, treatment of 15 with phenyliodine(III) diacetate (PIDA, PhI(OAc)$_2$) in a toluene/acetonitrile solvent system gave rise cleanly to a new product, 16, which was quite unstable. Alternatives to PIDA are other hypervalent iodine compounds such as phenyliodine(III)bis(trifluoroacetate) (PIFA), phenyliodine(III)sulfate, or dichloroiodobenzene. We note that formation of spiro ether 16a by ipso spirocyclization is apparently not at all competitive with the meta pathway leading from 15 to 16. Such an ipso pathway is inherent in the Becker-Adler reaction and analogs thereof. Evidently, the proclivity for attack at the electron-rich methoxy-bearing carbon is dominant in the PIDA mediated cyclization.

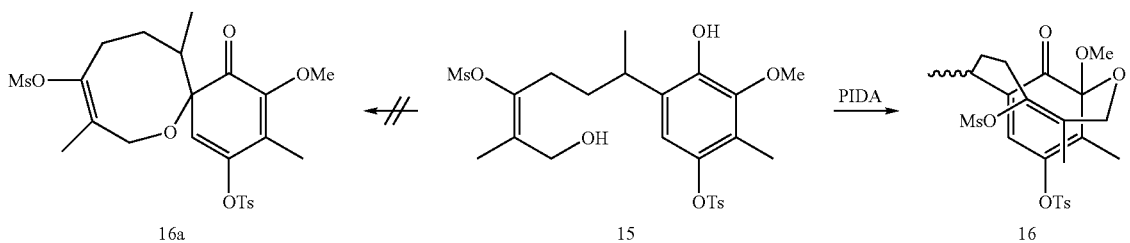

Of course, in reality, for a particular antipode, the methyl group defines the absolute configuration of the resultant cage-like latticework in structure 16. For convenience sake, we portray the intermediate by permuting the relative stereochemistry of the methyl bearing carbon.

As shown in Scheme 3, compound 16 failed to undergo the expected transannular Diels-Alder reaction (see target structure 17) under several sets of conditions. The surprising lability of 16 limited our options for permuting reaction conditions to accomplish transannular Diels-Alder reaction.

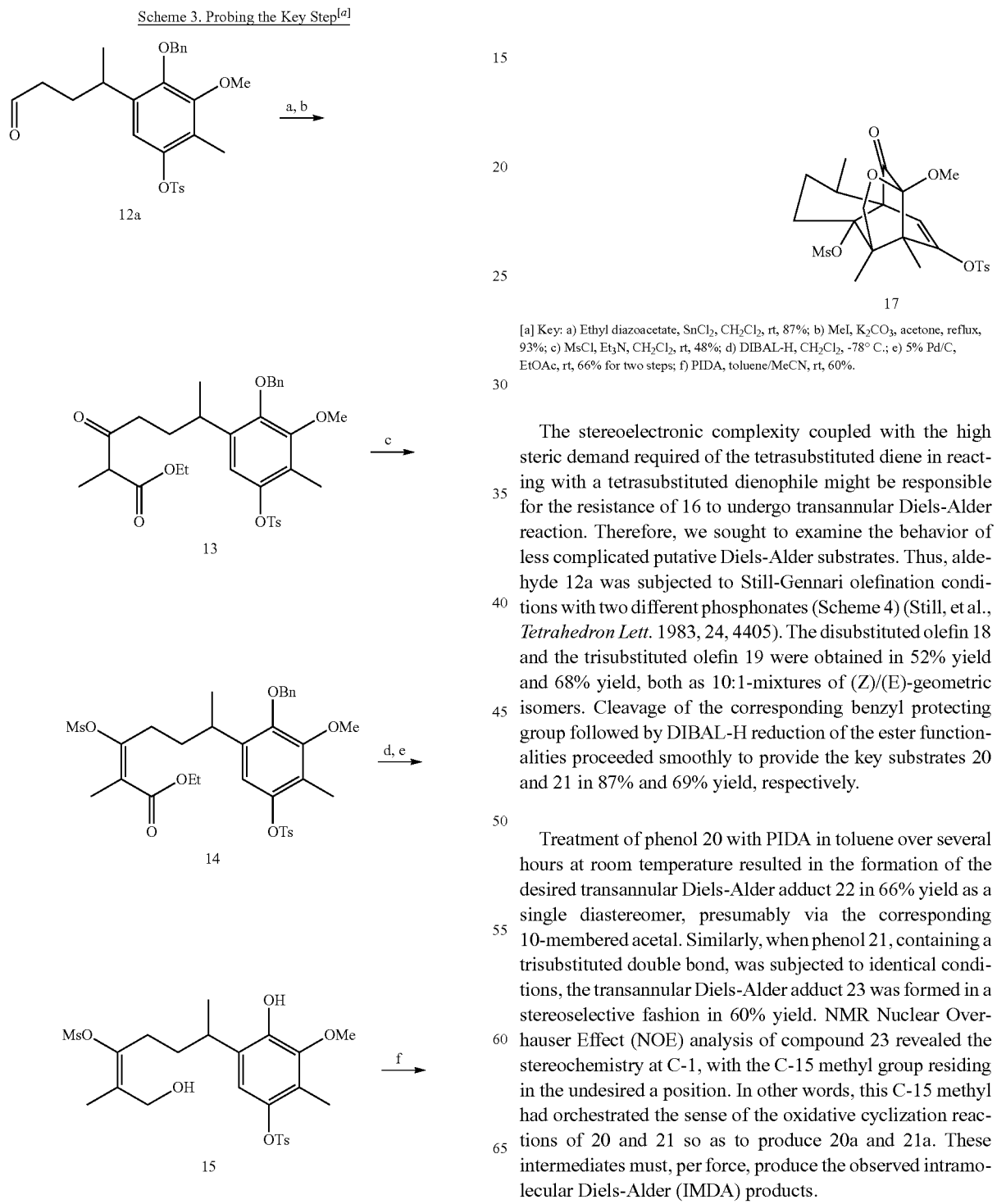

[a] Key: a) Ethyl diazoacetate, SnCl$_2$, CH$_2$Cl$_2$, rt, 87%; b) MeI, K$_2$CO$_3$, acetone, reflux, 93%; c) MsCl, Et$_3$N, CH$_2$Cl$_2$, rt, 48%; d) DIBAL-H, CH$_2$Cl$_2$, -78° C.; e) 5% Pd/C, EtOAc, rt, 66% for two steps; f) PIDA, toluene/MeCN, rt, 60%.

The stereoelectronic complexity coupled with the high steric demand required of the tetrasubstituted diene in reacting with a tetrasubstituted dienophile might be responsible for the resistance of 16 to undergo transannular Diels-Alder reaction. Therefore, we sought to examine the behavior of less complicated putative Diels-Alder substrates. Thus, aldehyde 12a was subjected to Still-Gennari olefination conditions with two different phosphonates (Scheme 4) (Still, et al., *Tetrahedron Lett.* 1983, 24, 4405). The disubstituted olefin 18 and the trisubstituted olefin 19 were obtained in 52% yield and 68% yield, both as 10:1-mixtures of (Z)/(E)-geometric isomers. Cleavage of the corresponding benzyl protecting group followed by DIBAL-H reduction of the ester functionalities proceeded smoothly to provide the key substrates 20 and 21 in 87% and 69% yield, respectively.

Treatment of phenol 20 with PIDA in toluene over several hours at room temperature resulted in the formation of the desired transannular Diels-Alder adduct 22 in 66% yield as a single diastereomer, presumably via the corresponding 10-membered acetal. Similarly, when phenol 21, containing a trisubstituted double bond, was subjected to identical conditions, the transannular Diels-Alder adduct 23 was formed in a stereoselective fashion in 60% yield. NMR Nuclear Overhauser Effect (NOE) analysis of compound 23 revealed the stereochemistry at C-1, with the C-15 methyl group residing in the undesired α position. In other words, this C-15 methyl had orchestrated the sense of the oxidative cyclization reactions of 20 and 21 so as to produce 20a and 21a. These intermediates must, per force, produce the observed intramolecular Diels-Alder (IMDA) products.

Scheme 4. Successful examples for the tandem oxidative dearomatization - transannular Diels-Alder reaction (TADA) sequence [a]
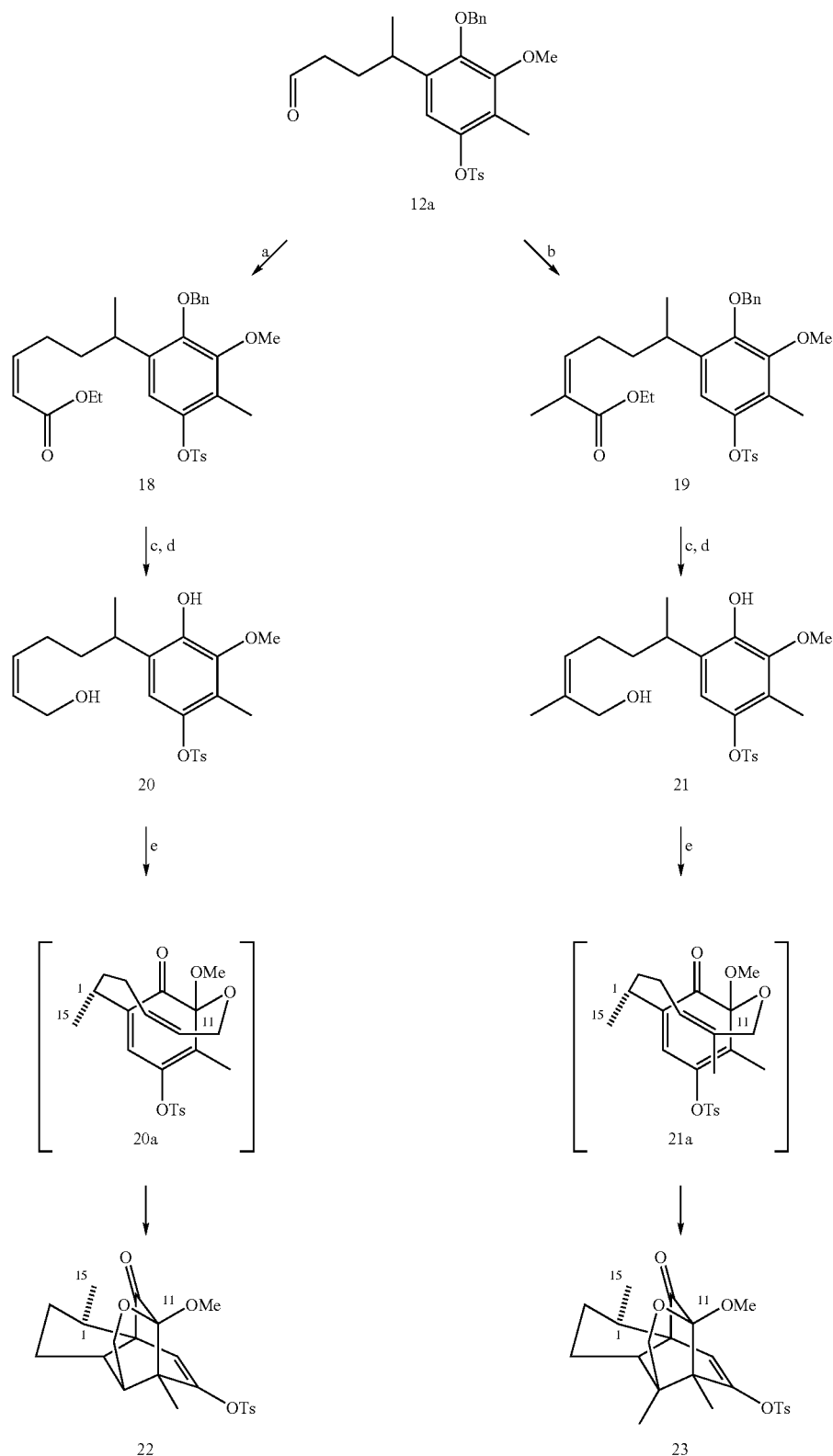
[a] Key: a) Phosphonate, KHMDS, 18-crown-6, THF, -78° C., 52%; b) Methyl phosphonate, KHMDS, 18-crown-6, THF, -78° C., 68%; c) BBr$_3$, CH$_2$Cl$_2$, -78° C.; d) DIBAL-H, CH$_2$Cl$_2$, -78° C., 87% (20) and 69% (21) over two steps; e) PIDA, toluene, rt, 66% (22) and 60% (23).

Experimental Procedures and Physical Data for Compounds 16, 22, and 23

Cyclic Acetal 16: To a solution of phenol 15 (7.5 mg, 0.014 mmol) in toluene (1 mL) at rt was added a solution of PIDA (5.3 mg, 0.016 mmol) in a 4:1 mixture of toluene:MeCN (1 mL) during 8 h via syringe pump. The reaction mixture was stirred for an additional 2 h at rt. The resulting clear, yellow solution was then diluted with DCM (30 mL), washed with saturated aqueous $Na_2S_2O_3$ (1×30 mL) and saturated aqueous $NaHCO_3$ (2×30 mL), then dried ($MgSO_4$) and concentrated. Purification by pTLC (1:1 hexane:diethyl ether) yielded compound 16 as a slightly yellow film (4.5 mg, 60%). $^1$H-NMR (300 MHz, $CDCl_3$) d 7.84 (d, J=8.3, 2H), 7.39 (d, J=8.3, 2H), 6.40 (s, 1H), 4.13 (d, J=14.1, 1H), 4.02 (d, J=14.1, 1H), 3.24 (s, 3H), 3.12 (s, 3H), 2.86 (m, 1H), 2.48 (s, 3H), 2.36 (m, 1H), 2.11 (m, 1H), 1.69 (s, 3H), 1.62 (s, 3H), 1.01 (d, J=6.9, 3H).

Cycloadduct 22: To a solution of phenol 20 (13 mg, 0.031 mmol) in toluene (1 mL) at rt was added a solution of PIDA (13 mg, 0.043 mmol) in a 4:1 mixture of toluene:MeCN (1 mL) during 4 h via syringe pump. At the end of the addition, the reaction was found to be complete. The reaction mixture was concentrated without workup and the residue was purified by preparatory thin layer chromatography (pTLC) (1:1 hexane:diethyl ether). Compound 22 was isolated as a slightly yellow film (8.5 mg, 66%). $^1$H-NMR (300 MHz, $CDCl_3$) d 7.79 (d, J=8.3, 2H), 7.37 (d, J=8.1, 2H), 5.77 (s, 1H), 4.12 (dd, $J_{gem}$=8.9, $J_{vie}$=4.2, 1H), 3.76 (d, J=8.9, 1H), 3.51 (s,3H), 2.81 (m, 1H), 2.46 (s,3H), 2.13 (m, 2H), 1.88 (m, 1H), 1.65 (m, 2H), 1.22 (s, 3H), 0.88 (d, J=7.1, 3H); $^{13}$C-NMR (125 MHz, $CDCl_3$) d 201.66, 148.97, 145.69, 132.63, 129.78, 128.65, 116.95, 100.27, 66.29, 60.02, 54.36, 52.50, 47.93, 41.68, 34.26, 27.24, 25.83, 21.72, 18.86, 12.26.

Cycloadduct 23: To a solution of phenol 21 (5.4 mg, 0.012 mmol) in toluene (1 mL) at rt was added a solution of PIDA (4.8 mg, 0.015 mmol) in a 4:1 mixture of toluene:MeCN (1 mL) during 4 h via syringe pump. At the end of the addition, the reaction was found to be complete. The reaction mixture was concentrated without workup and the residue was purified by pTLC (1:1 hexane:diethyl ether). Compound 23 was isolated as a slightly yellow film (3.2 mg, 60%). $^1$H-NMR (300 MHz, $CDCl_3$) d 7.80 (d, J=8.4, 2H), 7.36 (d, J=8.4, 2H), 5.87 (s, 1H), 3.73 (m, 2H), 3.50 (s, 3H), 2.80 (m, 1H), 2.46 (s, 3H), 2.14 (m, 1H), 1.62 (m, 1H), 1.52 (m, 1H), 1.12 (s, 3H), 0.94 (s, 3H), 0.91 (d, J=7.2, 3H); $^{13}$C-NMR (125 MHz, $CDCl_3$) d 202.00, 149.19, 146.08, 133.06, 130.21, 129.10, 116.21, 101.2, 72.18, 59.93, 55.63, 55.21, 54.50, 44.68, 34.41, 30.11, 27.65, 25.49, 22.13, 19.38, 9.54.

Conclusion

Having shown that both the di- and trisubstituted olefins do indeed undergo stereospecific oxidative dearomatization followed by transannular Diels-Alder, in contrast to the tetrasubstituted system in 16, we proceeded to reduce the complexity of the key sequence: instead of constructing all four rings of tashironin in a single transformation, we built three of the four rings by the oxidative dearomatization-transannular Diels-Alder cascade and then closing the fourth ring in subsequent transformations. Following this logic, the [2.2.2]bicyclic ring system is formed concomitantly either with the fused cyclopentane ring or with the 5-membered acetal. These approaches are exemplified in Examples 2 and 3.

Example 2

Formation of the Fused Cyclopentane Ring

In one approach, aldehyde 12b was converted to terminal alkyne 24 in 65% yield using the Bestmann reagent (Scheme 5) (Muller, et al., Synlett 1996 521; Ohira, Synth. Commun. 1989 19, 561). Phenol 25 was revealed in 90% yield after HCl-mediated removal of the MOM group. Exposure of phenol 25 to PIDA in MeOH at room temperature presumably led to the formation of the corresponding masked o-quinone, which underwent the desired transannular Diels-Alder reaction upon heating to afford 26 diastereoselectively in 85% yield (ds>95%). In the transformation from 25 to 26, any alkyl alcohol can be used instead of MeOH.

We were able to obtain single crystals of 26. X-ray analysis led to a decisive structural verification, revealing the relative configuration of the two quarternary stereocenters C-6/C-9 and the tertiary stereocenter C-1 as shown in Scheme 5. Crystallographic data (excluding structural data) for compound 26 have been deposited with the Cambridge Crystallographic Data Centre (CCDC) as Deposition No. CCDC 230898).

Scheme 5. Synthesis of Acetal 26[a]

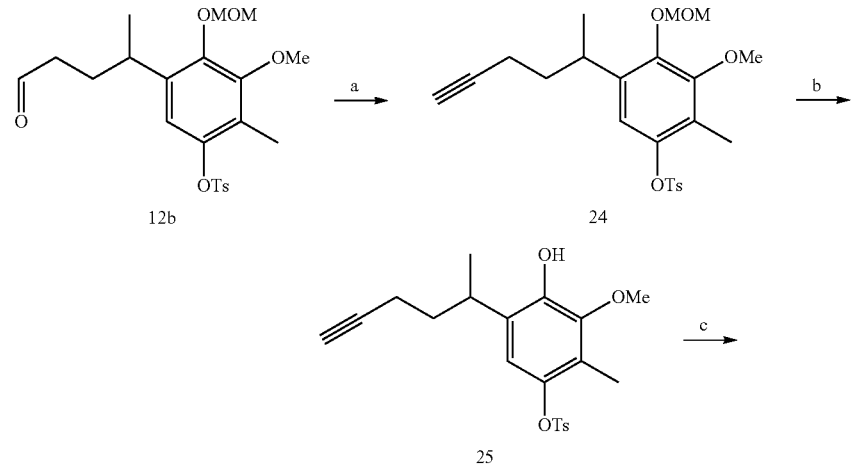

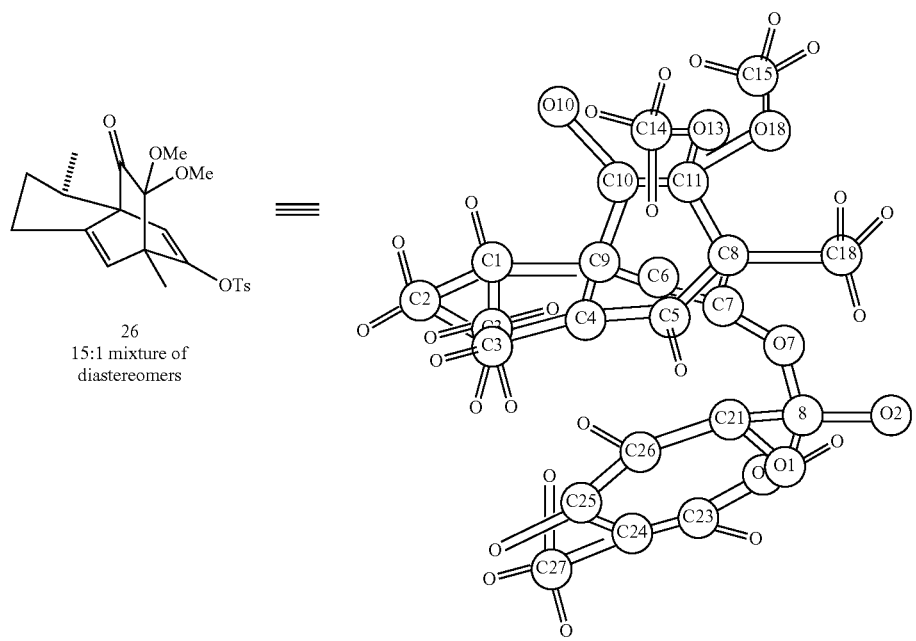

[a] Key: a) Bestmann reagent, K₂CO₃/MeOH, rt, 65%; b) HCl, MeOH, rt, 90%; c) PIDA, MeOH, rt, then toluene, reflux, 85%.

Experimental Procedures and Physical Data for Compound 26

Cycloadduct 26: To a solution of phenol 25 (78 mg, 0.201 mmol) in MeOH (4 mL) at rt was added a solution of PIDA (78 mg, 0.241 mmol) in MeOH (1.5 mL) during 1 h. The reaction mixture was then quenched with a mixture of saturated aqueous NaHCO₃ and saturated aqueous Na₂S₂O₃ then diluted with Et₂O. The organic layer was separated and the aqueous layer was extracted with Et₂O (3×). The combined organic layers were dried (MgSO₄) and concentrated under reduced pressure. The residual oil was dissolved in toluene (6 mL), heated to reflux for 20 min, then concentrated under reduced pressure. Purification of the crude product by fractional crystallization (FC) (hexane/EtOAc 2:1) afforded cycloadduct 26 (72 mg, 85%) as a white crystalline solid (de>95%). M.p. 67-69° C.; $^1$H-NMR (500 MHz, CDCl₃) d 7.76 (d, J=8.3, 2H), 7.33 (d, J=8.1, 2H), 5.77 (s, 1H), 5.56 (t, J=1.7, 1H), 3.33 (s, 3H), 3.25 (s, 3H), 2.83-2.77 (m, 1H), 2.45 (s, 3H), 2.33-2.29 (m, 2H), 1.92-1.87 (m, 1H), 1.56-1.50 (m, 1H), 1.33 (s, 3H), 0.98 (d, J=7.2, 3H); $^{13}$C-NMR (125 MHz, CDCl₃) d 195.19, 155.65, 150.70, 145.44, 132.63, 129.58, 128.69, 127.40, 111.33, 93.00, 67.31, 53.67, 53.51, 53.41, 34.72, 31.22, 26.54, 21.67, 15.80, 12.16; MS (ESI) 441 [M+Na⁺]; HRMS (FAB) calcd. for C₂₂H₂₆O₆SNa [M+Na⁺] 441.1348, found 441.1347.

Conclusion

The completion of the synthesis of debenzoyltashironin through this route requires the installation of functional handles in the Diels-Alder precursor to allow for the inversion of the stereochemistry at C-1 as well as for the closing of the 5-membered acetal.

Example 3

Formation of the 5-Membered Acetal

In an alternate approach, we sought to install the 5-membered acetal in conjunction with the [2.2.2]bicyclic ring system through an intermolecular trapping of an allenyl alcohol by oxidative dearomatization and a subsequent Diels-Alder reaction with the internal olefin of the allenol. This proposed IMDA cycloaddition raised obvious issues of regioselectivity. Although we were confident that the internal olefin of the allene would react preferentially due to the geometry of the transition state, predictions as to whether the reaction would give the desired 5-membered acetal Diels-Alder adduct 30 or the 6-membered acetal ("twisted") product 29 were less obvious (Scheme 6). In practice, phenol 27 was constructed in nine steps from the commercially available vanillyl alcohol 3a in 20% overall yield. Following treatment of 27 with PIDA in the presence of 5 equivalents of allenyl alcohol 28, the undesired "twisted" Diels-Alder adduct 29 was obtained (as shown by NOE studies) (Scheme 6) (Isaac, et al., *J. Chem. Soc. Chem. Comm.* 1995, 1003).

Scheme 6. "Twisted" Diels-Alder Product 29[a]

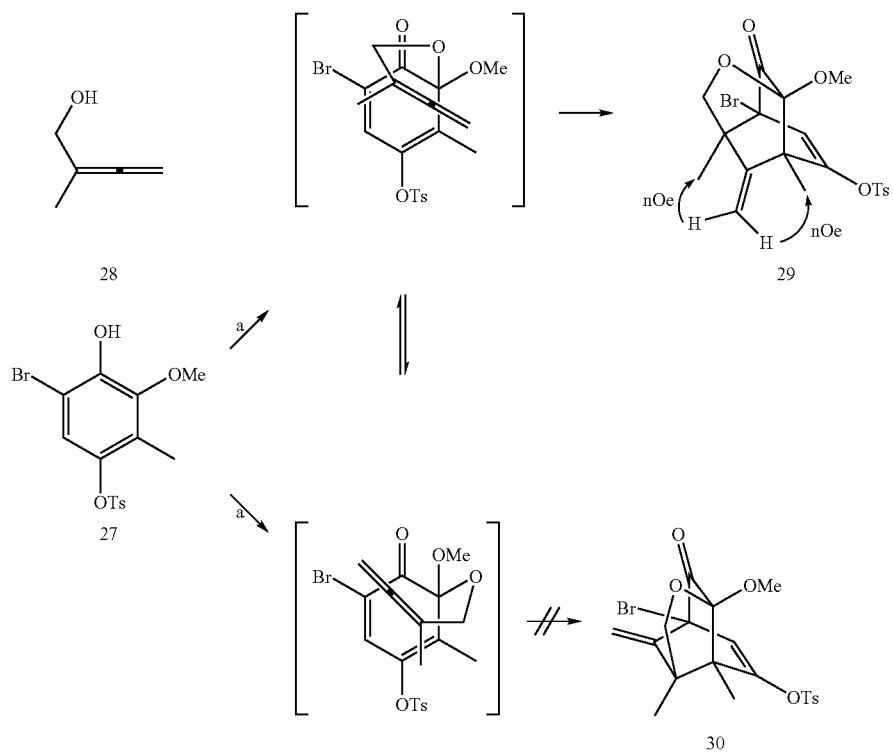

[a] Key: a) allenyl alcohol 28, PIDA, toluene, rt, 69%.

Experimental Procedures and Physical Data for Compound 29

Cycloadduct 29: To a solution of phenol 27 (25 mg, 0.064 mmol) and allenyl alcohol 28 (27 mg, 0.32 mmol, 5 eq.) in toluene (0.5 mL) at rt was added a solution of PIDA (36 mg, 0.084 mmol) in 4:1 toluene:MeCN (1 mL) during 4 h. The reaction mixture was stirred at rt for an additional 4 h, then diluted with $CH_2Cl_2$ (30 mL), and washed with saturated aqueous $Na_2S_2O_3$ (1×30 mL) and saturated aqueous $NaHCO_3$ (1×30 mL). The organic layer was dried ($MgSO_4$) and concentrated under reduced pressure. Purification of the crude product by pTLC (hexane/$Et_2O$ 1:1) afforded cycloadduct 29 (20.5 mg, 69%) as a yellow film. $^1$H-NMR (300 MHz, $CDCl_3$) d 7.71 (d, J=8.3, 2H), 7.37 (d, J=8.3, 2H), 5.83 (s, 1H), 4.92 (s, 1H), 4.88 (s, 1H), 3.73 (d, J=9.5, 1H), 3.53 (s, 3H), 3.41 (d, J=9.5, 1H), 2.48 (s, 3H), 1.27 (s, 3H), 1.07 (s, 3H); $^{13}$C-NMR (300 MHz, $CDCl_3$=77.0 ppm) d 194.69, 151.28, 151.12, 146.02, 131.59, 129.96, 128.72, 114.96, 104.09, 73.93, 69.52, 55.21, 54.03, 45.25, 21.74, 18.05, 8.63; HRMS (FAB) calcd. For $C_{20}H_{21}BrO_6Sna$ [M+H$^+$] 469.0321, found 469.0329.

Example 4

Completion of the Synthesis of Debenzoyltashironin

Four different methods of completing the synthesis of debenzoyltashironin and other tashironin analogs are shown in Schemes 7 A-D.

Scheme 7A

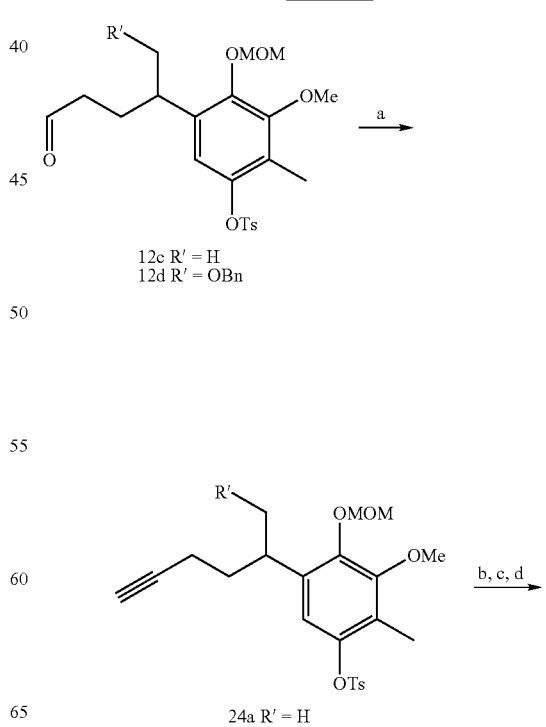

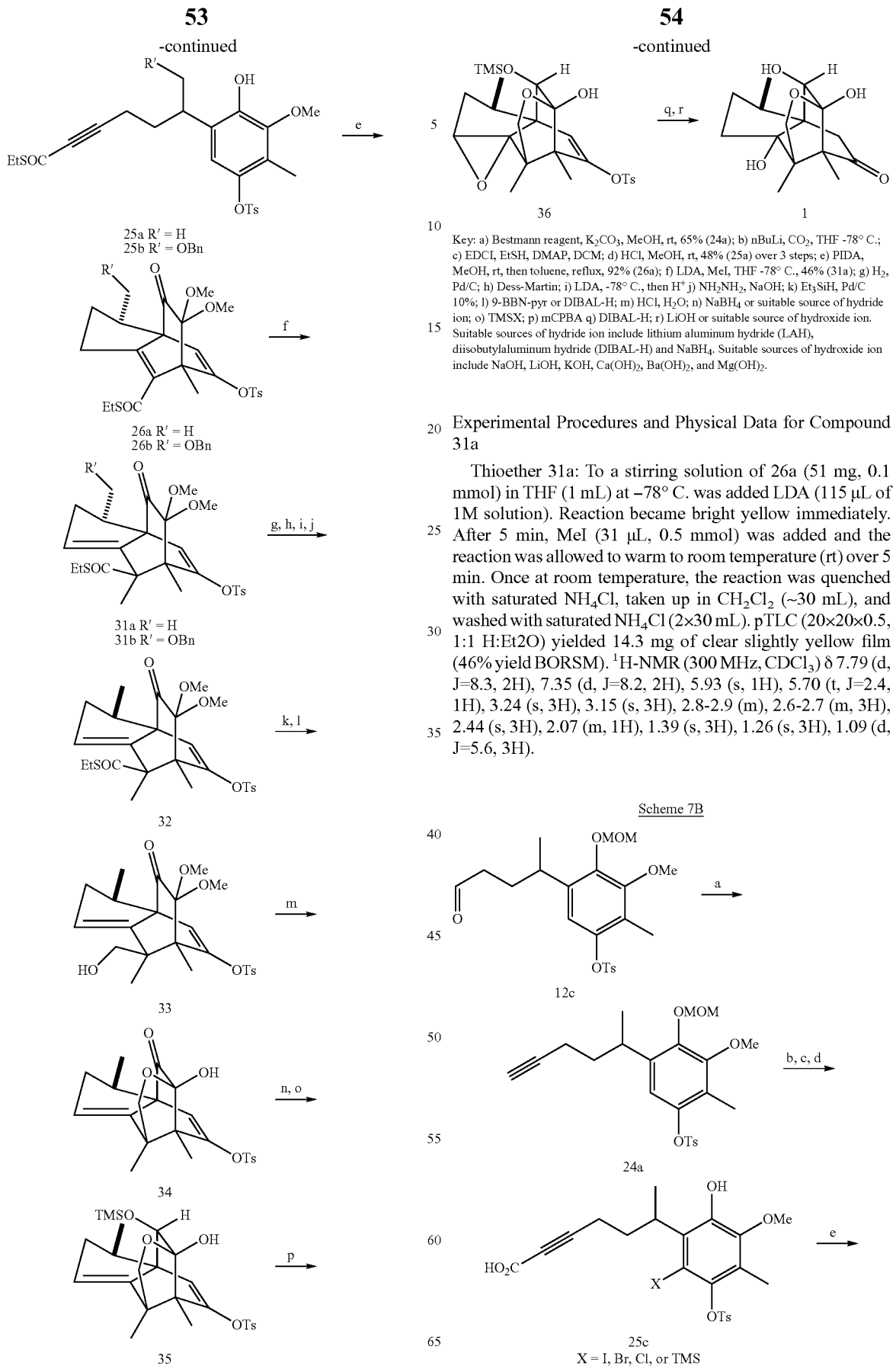

Key: a) Bestmann reagent, K$_2$CO$_3$, MeOH, rt, 65% (24a); b) nBuLi, CO$_2$, THF -78° C.; c) EDCI, EtSH, DMAP, DCM; d) HCl, MeOH, rt, 48% (25a) over 3 steps; e) PIDA, MeOH, rt, then toluene, reflux, 92% (26a); f) LDA, MeI, THF -78° C., 46% (31a); g) H$_2$, Pd/C; h) Dess-Martin; i) LDA, -78° C., then H$^+$ j) NH$_2$NH$_2$, NaOH; k) Et$_3$SiH, Pd/C 10%; l) 9-BBN-pyr or DIBAL-H; m) HCl, H$_2$O; n) NaBH$_4$ or suitable source of hydride ion; o) TMSX; p) mCPBA q) DIBAL-H; r) LiOH or suitable source of hydroxide ion. Suitable sources of hydride ion include lithium aluminum hydride (LAH), diisobutylaluminum hydride (DIBAL-H) and NaBH$_4$. Suitable sources of hydroxide ion include NaOH, LiOH, KOH, Ca(OH)$_2$, Ba(OH)$_2$, and Mg(OH)$_2$.

Experimental Procedures and Physical Data for Compound 31a

Thioether 31a: To a stirring solution of 26a (51 mg, 0.1 mmol) in THF (1 mL) at −78° C. was added LDA (115 µL of 1M solution). Reaction became bright yellow immediately. After 5 min, MeI (31 µL, 0.5 mmol) was added and the reaction was allowed to warm to room temperature (rt) over 5 min. Once at room temperature, the reaction was quenched with saturated NH$_4$Cl, taken up in CH$_2$Cl$_2$ (~30 mL), and washed with saturated NH$_4$Cl (2×30 mL). pTLC (20×20×0.5, 1:1 H:Et2O) yielded 14.3 mg of clear slightly yellow film (46% yield BORSM). $^1$H-NMR (300 MHz, CDCl$_3$) δ 7.79 (d, J=8.3, 2H), 7.35 (d, J=8.2, 2H), 5.93 (s, 1H), 5.70 (t, J=2.4, 1H), 3.24 (s, 3H), 3.15 (s, 3H), 2.8-2.9 (m), 2.6-2.7 (m, 3H), 2.44 (s, 3H), 2.07 (m, 1H), 1.39 (s, 3H), 1.26 (s, 3H), 1.09 (d, J=5.6, 3H).

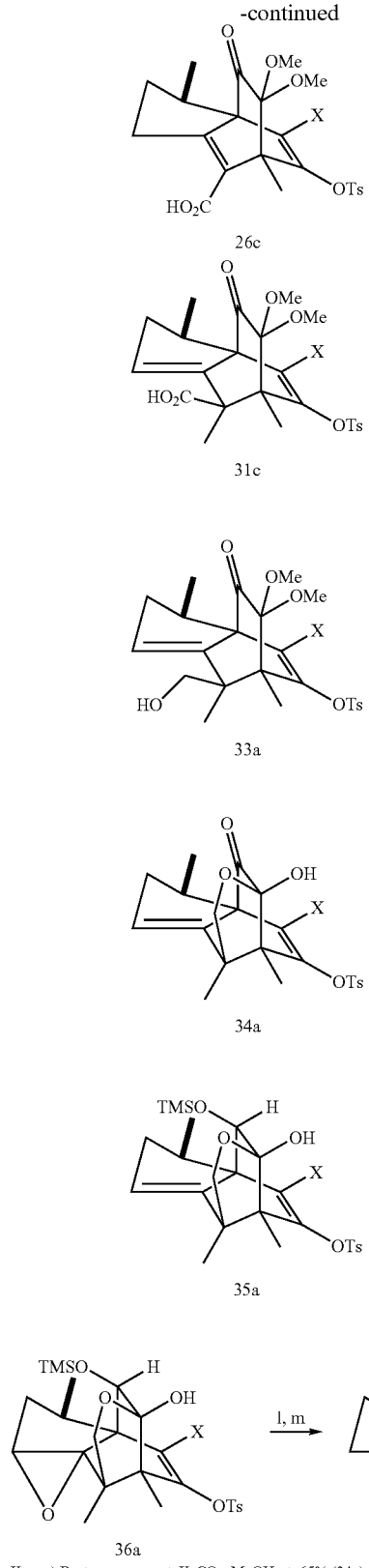
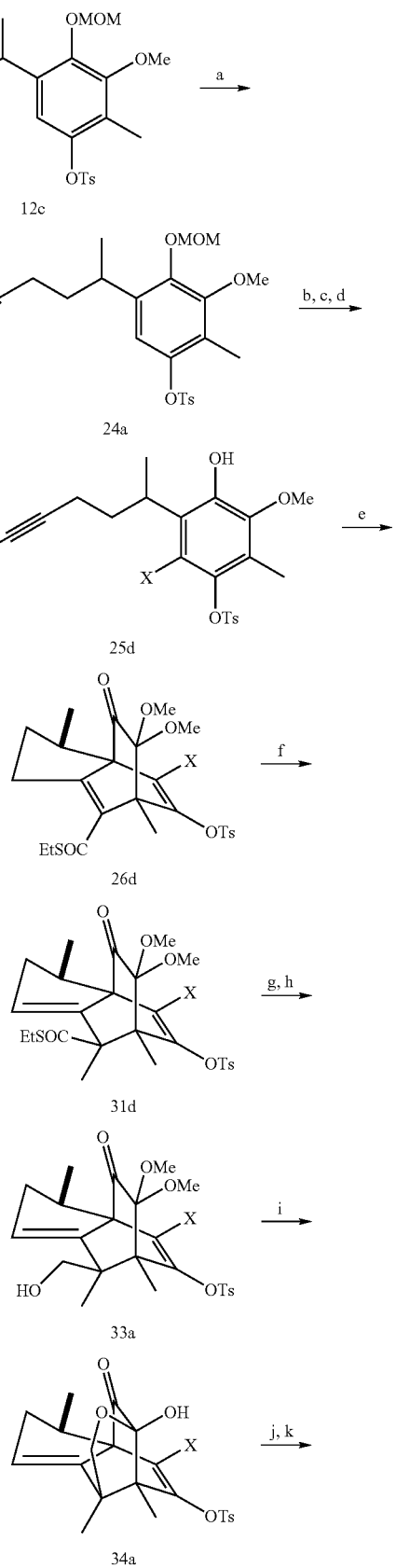

Scheme 7C

Key: a) Bestmann reagent, K₂CO₃, MeOH, rt, 65% (24a); b) nBuLi, CO₂, THF -78° C.; c) NIS or NBS or NCS or TMS-TMS, Pd; d) HCl, MeOH, rt; e) PIDA, MeOH; f) LDA, MeI, THF -78° C.; g) BH₃-THF, THF; h) HCl; i) H⁻; j) TMSCl; k) mCPBA; l) DIBAL-H or suitable source of hydride ion; m) NaOH or suitable source of hydroxide ion. Suitable sources of hydride ion include lithium aluminum hydride (LAH), diisobutylaluminum hydride (DIBAL-H) and NaBH₄. Suitable sources of hydroxide ion include NaOH, LiOH, KOH, Ca(OH)₂, Ba(OH)₂, and Mg(OH)₂.

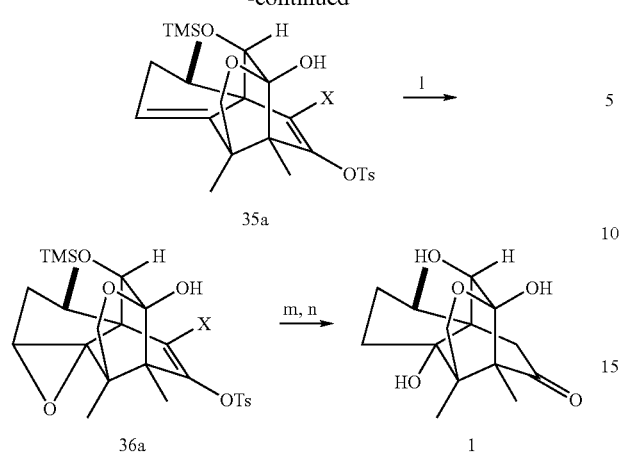

Key: a) Bestmann reagent, K₂CO₃, MeOH, rt, 65% (24a); b) nBuLi, CO₂, THF -78° C.; c) i) EDCI, EtSH, DMAP, DCM, ii) NIS or NBS or NCS or TMS-TMS; d) HCl, MeOH, rt; e) PIDA, MeOH; f) LDA, MeI, THF -78° C.; g) Et₃SiH, Pd/C 10%; h) NaBH₄ 9-BBN-pyr or; H⁻; i) HCl; j) H⁻; k) TMSCl; l) mCPBA; m) DIBAL-H or suitable source of hydride ion; n) i) NaOH or suitable source of hydroxide ion. ii) Zn or (PhSe)₂ or NaI. Suitable sources of hydride ion include lithium aluminum hydride (LAH), diisobutylaluminum hydride (DIBAL-H) and NaBH₄. Suitable sources of hydroxide ion include NaOH, LiOH, KOH, Ca(OH)₂, Ba(OH)₂, and Mg(OH)₂.

Scheme 7D

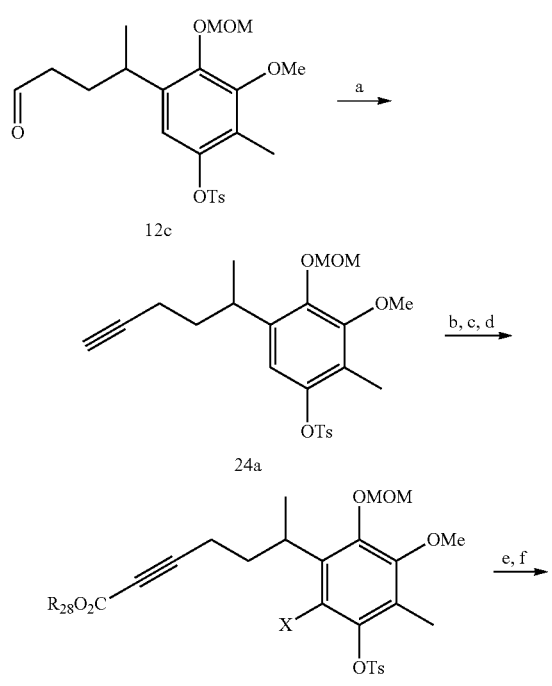

X = I, Br, Cl, TMS

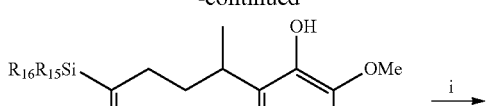

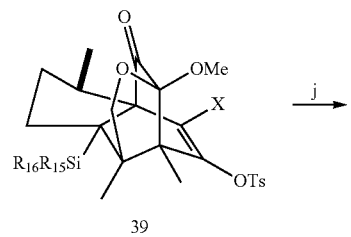

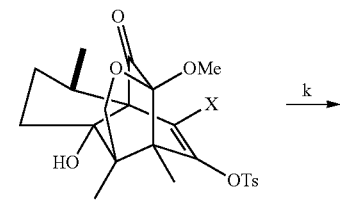

Key: a) Bestmann reagent, K₂CO₃, MeOH, rt, 65% (24a); b) nBuLi, CO₂, THF -78° C.; c) i) EDCI, ROH, DMAP, DCM, ii) NIS or NBS or NCS or TMS-TMS; d) HCl, MeOH, rt; e) R₁₆R₁₅SiCuLi, then I₂; f) Me₄Sn, Pd; g) DIBAL-H or suitable source of hydride ion; h) HCl i) PIDA j) H2O2, (C₁-C₄) alkyl or benzyl peroxide/NaOH; k) H⁺; l) NaOH or suitable source of hydroxide ion; R₂₈ is (C₁-C₄) alkyl; R₁₅ and R₁₆ are each independently are (C₁-C₄) alkyl, phenyl or furanyl. Suitable sources of hydride ion include lithium aluminum hydride (LAH), diisobutylaluminum hydride (DIBAL-H) and NaBH₄. Suitable sources of hydroxide ion include NaOH, LiOH, KOH, Ca(OH)₂, Ba(OH)₂, and Mg(OH)₂.

Example 5

Alternate Formation of Tetracyclic Core

In this synthesis, the bromo methylvanillin was protected with tert-butyldimethylsilane using TBSCl, imidazole, and dimethylamino pyridine (DMAP) in 74% yield. This compound was then treated to Baeyer-Villiger conditions (m-chloroperoxybenzoic acid, mCPBA) to yield a formate that is hydrolyzed with triethylamine (TEA) in methanolic solvent (MeOH/DCM). The new phenol was then tosylated with TsCl and amine base to yield compound number 80.

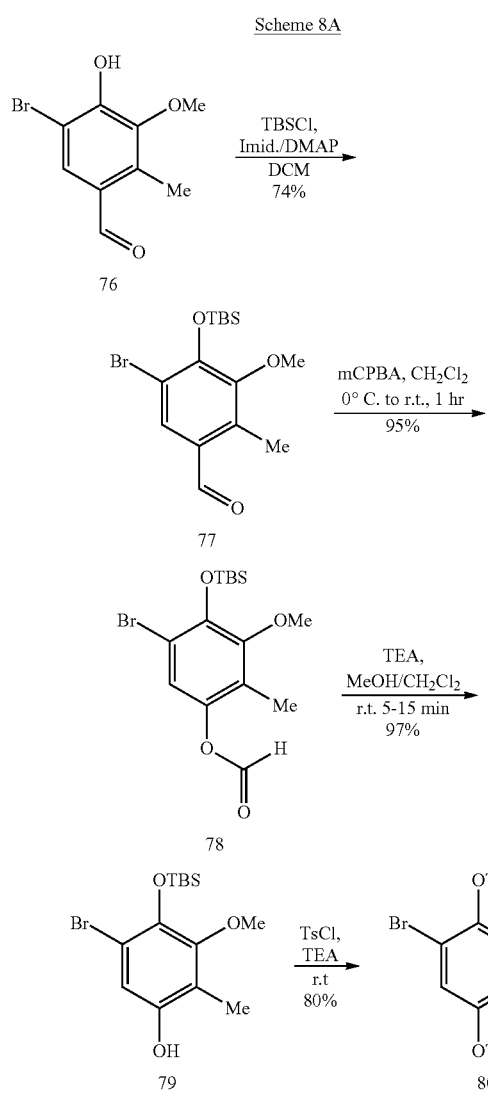
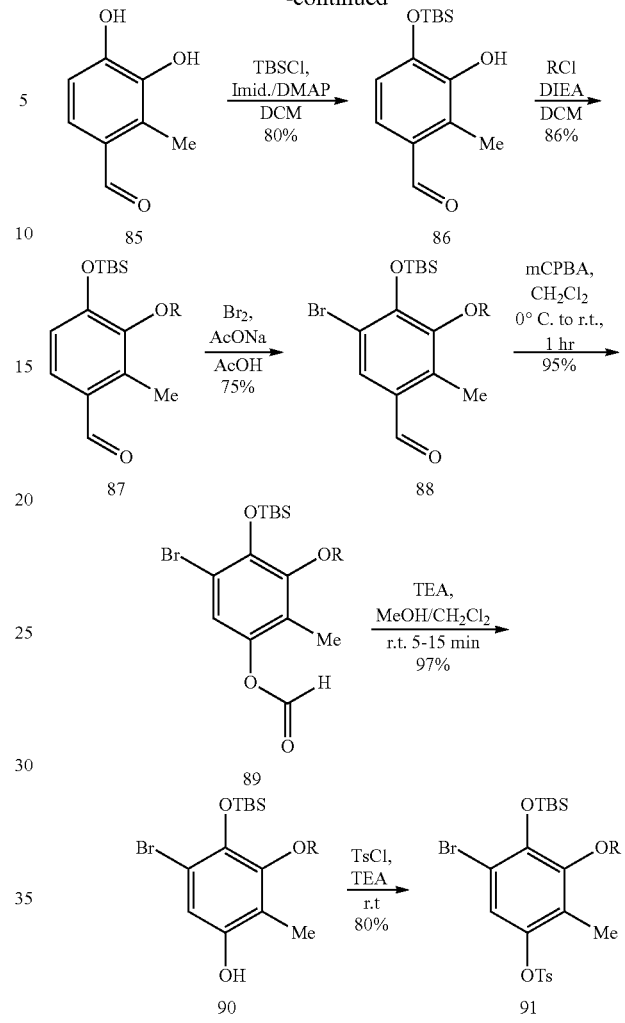

Example 6

Alternate Formation of the Carboskeleton of Tashironin

This scheme describes a new sequence to the carboskeleton of tashironin employing different reaction sequences and compounds than the previously described schemes. None of the intermediate compounds are expected to yield any specific biological result, but the final compound of the scheme, compound number 98, is an analog of debenzoylatashironin and based upon its relationship to debenzoyltashironin, compound number 98 is expected to have neurotrophic activity. From the beginning, a palladium-mediated "Stille" coupling yielded a new primary alcohol that was oxidized to a beta, gamma-unsaturated aldehyde in 98% and 99% yield, respectively. Base-mediated (BuLi) alkyne addition to this aldehyde, followed by mesylation of the resulting alcohol (MsCl and TEA) and cuprate addition of a higher-order cyano cuprate (also known as a Lipshutz cuprate) yielded a racemic allene. This allene is deprotected using tetrabutyl ammonium fluoride (TBAF) in acetic acid to yield a hydroxyphenol. This hydroxyphenol is the key intermediate for the synthesis.

When this hydroxyphenol was subjected to phenyliodo(diacetate) (PIDA), a 12-membered acetal ring was formed in situ, followed by a transannular-Diels-Alder reaction to get the carboskeleton of tashironin (the last compound of the scheme).

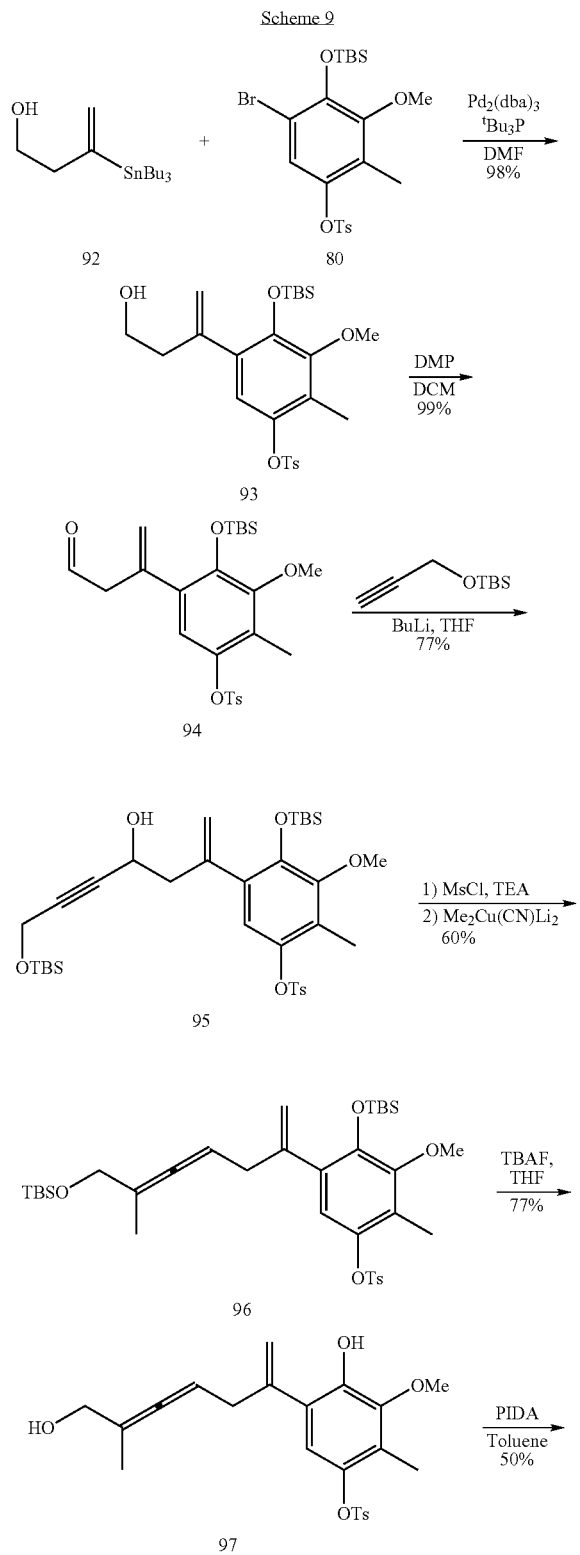

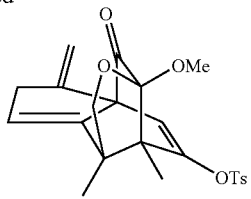

Example 7

Alternate Route to Natural Product and Formation of Analogs

This scheme describes a series of analogs en route to the natural product. Reduction of the ketone produced a secondary alcohol with a 7:1 diastereoselectivity. This selectivity can be adjusted experimentally by changing the nature of the reducing agent. Sodium borohydride gives 7:1, while lithium aluminum hydride provides a 1:1 mixture. Protection of this secondary alcohol with trimethylsilane was done in a 1:1 mixture of TMS-imidazole:$CH_2Cl_2$. A solvent system containing less TMS-imidazole resulted in a sluggish reaction. Once protected with trimethylsilane, one of the three double bonds was selectively epoxidized on the face opposite the TMS protecting group. The exomethylene was then diastereoselectively reduced using standard hydrogen and palladium on carbon conditions. Again, the selectivity is accomplished by steric occlusion by the TMS group on the "top" surface of the olefins. The epoxide was then reductively opened and the tosyl enol ether reductively cleaved using lithium di-tert-butyldiphenyl (LiDBB) to yield the more substituted alcohol and a ketone, respectively. (There exist conditions that would result in the opening of epoxide to yield the less substituted alcohol.) Strong acids then remove the remaining TMS and Me protecting groups to yield the purported neurotrophic factor, debenzoyltashironin.

Since the methyl group of the OMe was so difficult to remove using the chemistry described in this scheme, additional chemistry is described in Scheme 8B above that describes a method for incorporating a more labile protecting group (methyl methoxyether (MOM) is described in scheme 8B). Starting from commercially available methyl catechol, dimethyl sulfate was used to methylate the two phenols. N-Bromosuccinamide (NBS) in acetonitrile (MeCN) was then used to brominate the aromatic ring at the 4-position. Lithium-halogen exchange with butyl lithium (BuLi), followed by quenching with dimethylformamide (DMF) yielded the 4-aldehyde. Boron tribromide ($BBr_3$) removal of the methyl groups revealed the catechol once again. Here, selective protection of one or the other phenol is possible. In Scheme 8A, TBS and MOM are used, but just about any combination would be acceptable. Once protected, another aromatic bromination was carried out using bromine in acetic acid to yield the bromide described in Scheme 8A, albeit with a more labile protecting group than methyl.

Scheme 10

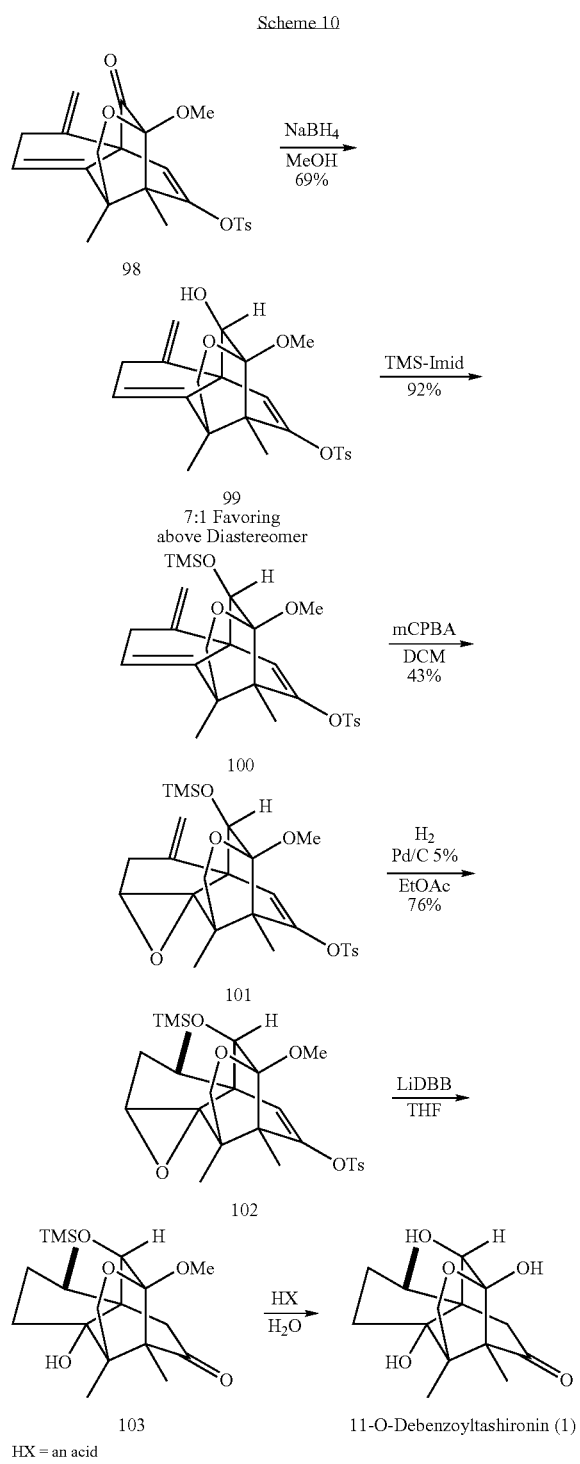

Discussion

We have shown herein the highly concise synthesis of the tetracyclic ring system that forms the core of 11-0-debenzoyltashironin. The synthesis was achieved by a Pelter-Tamura oxidation resulting in the trapping of a tethered allylic alcohol, followed by a transannular Diels-Alder reaction. We have also shown that this reaction sequence is viable for the efficient construction of related, rather complex [2.2.2]-bicyclic compounds.

The synthesis of the [2.2.2]-bicyclic core of the neurotrophic factor 11-0-debenzoyltashironin (1) has been achieved by an oxidative dearomatization-transannular Diels-Alder cascade. The reaction sequence is also valuable for the efficient construction of related, complex [2.2.2]-bicyclic compounds.

The tandem oxidative dearomatization-transannular Diels-Alder reaction sequence is used in any one of four different methods to complete the synthesis of debenzoyltashironin and tashironin analogs.

Using the aforementioned processes produces Tashironin, debenzoyltashironin and other tashironin derivative compositions free of biological material of *illicium tashiroi*, which biological material is otherwise necessarily present, if only in trace amounts, when tashironin is isolated from the tashiroi plant. Thus, a composition "free" of biological material of *illicium tashiroi* according to this invention contains absolutely no such biological material.

Tashironin can be used to treat cancer patients alone or in combination with other therapeutic agents. Some patients undergoing treatment with anticancer agents experience a tingling sensation. The tingling has been attributed to damage to neurites, which damage is possibly caused by the anticancer agents. In the past, Granulocyte Colony Stimulating Factor (GCSF) has been used with chemotherapy to treat patients experiencing this type of tingling. Thus, it is beneficial to administer tashironin or its derivatives to patients undergoing chemotherapy in an amount effective to treat or inhibit the damage to neurites associated with chemotherapy.

Tashironin can be used to treat patients with diabetes alone or in combination with other therapeutic agents. Some diabetes patients experience a tingling sensation. The tingling has been attributed to damage to neurites, which damage is possibly caused by the diabetes. Thus, it is beneficial to administer tashironin or its derivatives to patients with diabetes in an amount effective to treat or inhibit the damage to neurites associated with diabetes.

What is claimed is:

1. A compound having the structure of the formula (72)

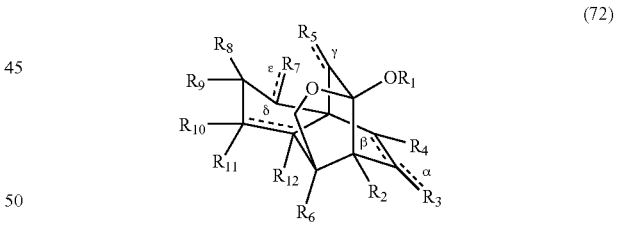

wherein, $R_1$ is H or Bz when no more than three of $R_8$, $R_9$, $R_{10}$ and $R_{11}$ are H, or
$R_1$ is Bn, ($C_1$-$C_4$) alkyl, or $CF_3$;
$R_2$ is H, ($C_1$-$C_4$) alkyl, halide, OC(O)($C_1$-$C_4$)alkyl, OC(O) Ph, or $OCF_3$;
$R_3$ is p-toluene sulfonyloxy, methane sulfonyloxy, C(O)($C_1$-$C_4$)alkyl, or OC(O)($C_1$-$C_4$)alkyl, bond α is a single bond, and bond β is a double bond or
$R_3$ is O, bond α is a double bond and bond β is a single bond;
$R_4$ is H, I, Br, Cl, Si($CH_3$)$_3$, ($C_1$-$C_4$)alkyl, or $OCF_3$,
$R_5$ is OH, OSi($CH_3$)$_3$, O($C_1$-$C_4$) alkyl, or $OCF_3$, and bond γ is a single bond, or
$R_5$ is O and bond γ is a double bond;
$R_6$ is H, ($C_1$-$C_4$) alkyl, or $CF_3$;

$R_7$ is H, OH, $(C_1\text{-}C_4)$alkyl, $CH_2OBn$, $CH_2O(C_1\text{-}C_4)$alkyl, $CH_2OH$, halide, $CH_2OCF_3$ or $OCF_3$ and bond $\epsilon$ is a single bond, or $R_7$ is $CH_2$ and bond $\epsilon$ is a double bond;

$R_8$, $R_9$, and $R_{10}$ are each independently H, $(C_1\text{-}C_4)$alkyl, halide, OH, or $OCF_3$;

$R_{11}$ is H, $(C_1\text{-}C_4)$alkyl, halide, OH, or $OCF_3$ and bond $\delta$ is a single bond;

$R_{12}$ is H, $(C_1\text{-}C_4)$alkyl, $O(C_1\text{-}C_4)$alkyl, p-toluene sulfonyloxy or methane sulfonyloxy, halide, OH, $OCF_3$, or $R_{15}R_{16}Si$, where $R_{15}$ and $R_{16}$ are each independently $(C_1\text{-}C_4)$alkyl, furanyl or Ph, and bond $\delta$ is a single bond;

$R_{11}$ together with $R_{12}$ and the carbons to which each is attached to form an oxirane moiety form an ether group and bond $\delta$ is a single bond; or $R_{11}$ and $R_{12}$ are absent and bond $\delta$ is a double bond.

2. The compound of claim 1 having the structure of the formula

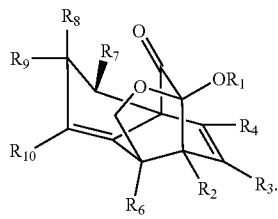

(64)

3. The compound of claim 2, wherein $R_1$, $R_4$, $R_8$, $R_9$, and $R_{10}$ are H, $R_2$, $R_6$, and $R_7$ are $CH_3$, and $R_3$ is p-toluene sulfonyloxy.

4. The compound of claim 2, wherein $R_1$, $R_8$, $R_9$, and $R_{10}$ are H, $R_2$, $R_6$, and $R_7$ are $CH_3$, $R_3$ is p-toluene sulfonyloxy and $R_4$ is I, Br, Cl, or $Si(CH_3)_3$.

5. The compound of claim 1 having the structure of the formula

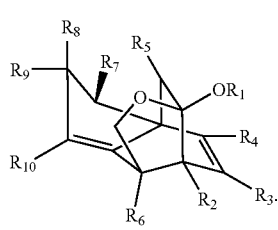

(65)

6. The compound of claim 5, wherein $R_1$, $R_4$, $R_8$, $R_9$, and $R_{10}$ are H, $R_2$, $R_6$ and $R_7$ are $CH_3$, $R_3$ is p-toluene sulfonyloxy, and $R_5$ iS $OSi(CH_3)_3$.

7. The compound of claim 5, wherein $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

8. The compound claim 1 having the structure of the formula

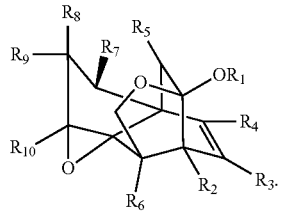

(66)

9. The compound of claim 8, wherein $R_1$, $R_4$, $R_8$, $R_9$, and $R_{10}$ are H, $R_2$, $R_6$ and $R_7$ are $CH_3$, $R_3$ is p-toluene sulfonyloxy and $R_5$ is $OSi(CH_3)_3$.

10. The compound of claim 8, wherein $R_1$, $R_8$, $R_9$, and $R_{10}$ are H, $R_2$, $R_6$ and $R_7$ are $CH_3$, $R_3$ is p-toluene sulfonyloxy, $R_4$ is I, Br, Cl, or $Si(CH_3)_3$, and $R_5$ is $OSi(CH_3)_3$.

11. The compound of claim 1 having the structure of formula

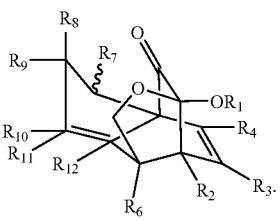

(68)

12. The compound of claim 11, wherein $R_1$, $R_2$, $R_6$, and $R_7$ are $CH_3$, $R_3$ is p-toluene sulfonyloxy, $R_4$ is I, Br, Cl, or $Si(CH_3)_3$, $R_8$, $R_9$, $R_{10}$, and $R_{11}$ are H, and $R_{12}$ is $R_{15}R_{16}Si$, wherein $R_{15}$ and $R_{16}$ are each independently $(C_1\text{-}C_4)$alkyl or Ph.

13. The compound of claim 1 having the structure of formula

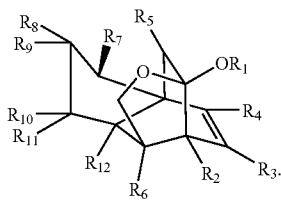

(69)

14. The compound of claim 13, wherein $R_1$, $R_2$, $R_6$, and $R_7$ are $CH_3$, $R_3$ is p-toluene sulfonyloxy, $R_4$ is I, Br, Cl, or $Si(CH_3)_3$, $R_5$ is $OSi(CH_3)_3$, $R_8$, $R_9$, $R_{10}$, and $R_{11}$ are H, and $R_{12}$ is OH.

15. The compound of claim 1, having the structure

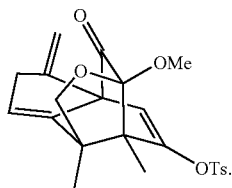

16. A pharmaceutical composition comprising the compound of any one of claim 1 and a pharmaceutically acceptable carrier.

17. A compound having the structure of the formula

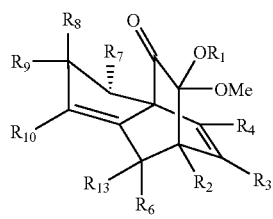

(63)

wherein $R_{13}$ is C(O)OH, C(O)O($C_1$-$C_4$)alkyl, or C(O)S ($C_1$-$C_4$) alkyl.

18. A composition comprising a compound having the structure of the formula

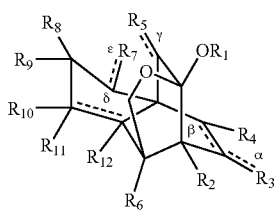

(72)

wherein,
$R_1$ is H, Bn, Bz, ($C_1$-$C_4$)alkyl, or $CF_3$,
$R_2$ is H, ($C_1$-$C_4$) alkyl, halide, OC(O)($C_1$-$C_4$)alkyl, OC(O)Ph, or $OCF_3$;
$R_3$ is p-toluene sulfonyloxy, methane sulfonyloxy, C(O)($C_1$-$C_4$)alkyl, or OC(O)($C_1$-$C_4$)alkyl, bond α is a single bond, and bond β is a double bond or
$R_3$ is O, bond α is a double bond and bond β is a single bond;
$R_4$ is H, I, Br, Cl, Si($CH_3$)$_3$, ($C_1$-$C_4$)alkyl, or $OCF_3$;
$R_5$ is OH, OSi($CH_3$)$_3$, O($C_1$-$C_4$) alkyl, or $OCF_3$, and bond γ is a single bond, or
$R_5$ is O and bond γ is a double bond;
$R_6$ is H, ($C_1$-$C_4$) alkyl, or $CF_3$;
$R_7$ is H, OH, ($C_1$-$C_4$)alkyl, $CH_2$OBn, $CH_2$O($C_1$-$C_4$)alkyl, $CH_2$OH, halide, $CH_2OCF_3$ or $OCF_3$ and bond ε is a single bond, or
$R_7$ is $CH_2$ and bond ε is a double bond;
$R_8$, $R_9$, and $R_{10}$ are each independently H, ($C_1$-$C_4$)alkyl, halide, OH, or $OCF_3$;
$R_{11}$ is H, ($C_1$-$C_4$)alkyl, halide, OH, or $OCF_3$ and bond δ is a single bond;
$R_{12}$ is H, ($C_1$-$C_4$)alkyl, O($C_1$-$C_4$)alkyl, p-toluene sulfonyloxy or methane sulfonyloxy, halide, OH, $OCF_3$, or $R_{15}R_{16}$Si, where $R_{15}$ and $R_{16}$ are each independently ($C_1$-$C_4$)alkyl, furanyl or Ph, and bond δ is a single bond;
$R_{11}$ together with $R_{12}$ and the carbons to which each is attached to form an oxirane moiety form an ether group and bond δ is a single bond; or
$R_{11}$ and $R_{12}$ are absent and bond δ is a double bond; and wherein the composition is free of biological material of *illicium tashiroi*.

19. A composition comprising a compound having the structure of the formula

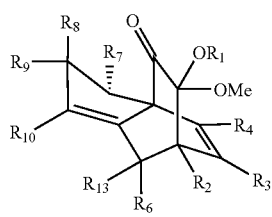

(63)

wherein $R_{13}$ is C(O)OH, C(O)O($C_1$-$C_4$)alkyl, or C(O)S ($C_1$-$C_4$) alkyl.

20. A compound having the structure of formula

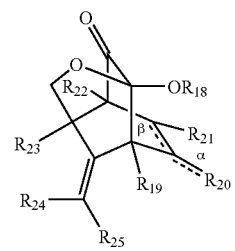

(73)

wherein, $R_{18}$ is H, ($C_1$-$C_4$)alkyl, or $CF_3$;
$R_{19}$ is H, O($C_1$-$C_4$)alkyl, ($C_1$-$C_4$)alkyl, halide, $OCF_3$, or $CF_3$;
$R_{20}$ is H, p-toluene sulfonyloxy, methane sulfonyloxy, C(O)($C_1$-$C_4$) alkyl, or OC(O)($C_1$-$C_4$)alkyl, and bond α is a single bond or $R_{20}$ is O and bond α is a double bond;
$R_{21}$, $R_{24}$, and $R_{25}$ are each independently H, O($C_1$-$C_4$) alkyl, ($C_1$-$C_4$) alkyl, halide, $OCF_3$, or $CF_3$;
$R_{22}$ is a halide, H, or ($C_1$-$C_4$)alkyl; and
$R_{23}$ is H, O($C_1$-$C_4$)alkyl, ($C_1$-$C_4$)alkyl, halide, $OCF_3$, $CF_3$ or Ph.

21. A process of producing a compound of the formula

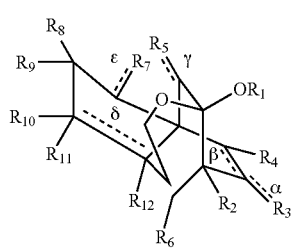

(72)

wherein,
$R_1$ is H, Bn, Bz, ($C_1$-$C_4$)alkyl, or $CF_3$;
$R_2$ is H, ($C_1$-$C_4$)alkyl, halide, OC(O)($C_1$-$C_4$)alkyl, OC(O)Ph, or $OCF_3$;

$R_3$ is p-toluene sulfonyloxy, methane sulfonyloxy, C(O)($C_1$-$C_4$)alkyl, or OC(O)($C_1$-$C_4$)alkyl, bond α is a single bond and bond β is a double bond, or $R_3$ is O, bond α is a double bond and bond β is a single bond;

$R_4$ is H, I, Br, Cl, Si($CH_3$)$_3$, ($C_1$-$C_4$)alkyl, or $OCF_3$;

$R_5$ is OH, OSi($CH_3$)$_3$, O($C_1$-$C_4$)alkyl, or $OCF_3$, and bond γ is a single bond, or $R_5$ is O and bond γ is a double bond;

$R_6$ is H, ($C_1$-$C_4$)alkyl, or $CF_3$;

$R_7$ is H, OH, ($C_1$-$C_4$)alkyl, $CH_2$OBn, $CH_2$O($C_1$-$C_4$)alkyl, $CH_2$OH, halide, $CH_2OCF_3$ or $OCF_3$ and bond ε is a single bond, or $R_7$ is $CH_2$ and bond ε is a double bond;

$R_8$, $R_9$, and $R_{10}$ are each independently H, ($C_1$-$C_4$)alkyl, halide, OH, or $OCF_3$; and $R_{11}$ and $R_{12}$ are each independently H, ($C_1$-$C_4$)alkyl, halide, OH, or $OCF_3$ and bond δ is a single bond, $R_{11}$ together with $R_{12}$ and the carbons to which each is attached to form an oxirane moiety form an ether group and bond δ is a single bond or $R_{11}$ and $R_{12}$ are absent and bond δ is a double bond, comprising subjecting a compound of the formula

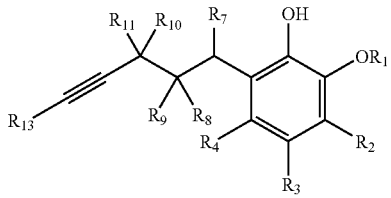

(71)

wherein $R_1$, $R_2$, $R_3$, $R_4$, $R_7$, $R_8$, $R_9$, $R_{10}$, and $R_{11}$ are defined as above; and $R_{13}$ is —C(O)OH, —C(O)O($C_1$-$C_4$)alkyl, or —C(O)S($C_1$-$C_4$)alkyl, to a tandem oxidative dearomatization-transannulation Diels-Alder reaction to obtain the compound.

22. A process of producing a compound of the formula

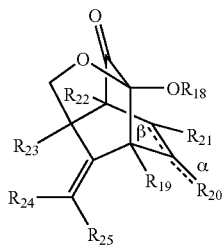

(73)

wherein, $R_{18}$ is H, ($C_1$-$C_4$)alkyl, or $CF_3$;

$R_{19}$ is H, O($C_1$-$C_4$)alkyl, ($C_1$-$C_4$)alkyl, halide, $OCF_3$, or $CF_3$;

$R_{20}$ is H, p-toluene sulfonyloxy, methane sulfonyloxy, C(O)($C_1$-$C_4$)alkyl, or OC(O)($C_1$-$C_4$)alkyl, bond α is a single bond and bond β is a double bond or $R_{20}$ is O, bond α is a double bond and bond β is a single bond;

$R_{21}$, $R_{24}$, and $R_{25}$ are each independently H, O($C_1$-$C_4$) alkyl, ($C_1$-$C_4$)alkyl, halide, $OCF_3$, or $CF_3$;

$R_{22}$ is a halide, H, or ($C_1$-$C_4$)alkyl; and $R_{23}$ is H, O($C_1$-$C_4$)alkyl, ($C_1$-$C_4$)alkyl, halide, $OCF_3$, $CF_3$ or Ph comprising reacting a compound of the formula

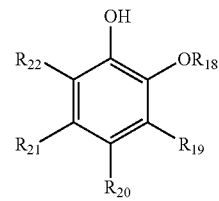

(74)

with a compound of the formula

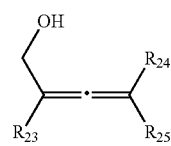

(75)

to obtain the compound.

23. A process of producing a compound of the formula

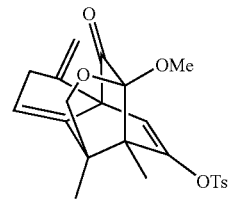

comprising a) reacting the compounds of the formulae

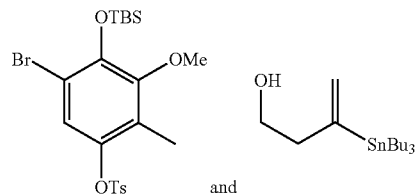

wherein $R_1$ are defined as above, with $Pd_2(dba)_3$, $^tBu_3P$, and DMF to obtain a compound of the formula

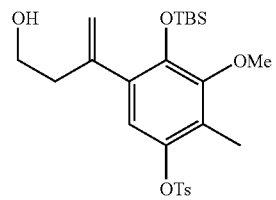

b) reacting the product of step a) with DMP and DCM to obtain a compound of the formula

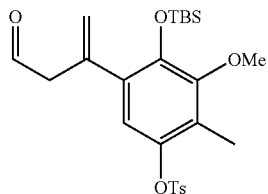

c) reacting the product of step b) with a compound of the formula

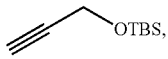

BuLi, and THF to obtain a compound of the formula

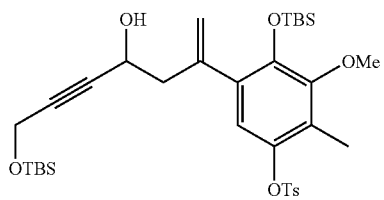

d) reacting the product of step c) first with MsCl and TEA and then with $Me_2Cu(CN)Li_2$ to obtain a compound of the formula

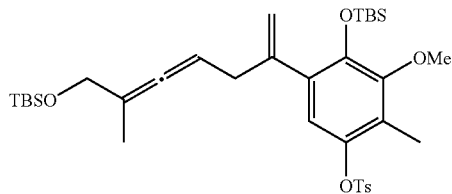

e) reacting the product of step d) with TBAF and THF to obtain a compound of the formula

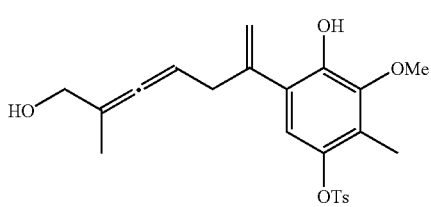

f) and reacting the product of step e) with PIDA and Toluene to thereby obtain the compound.

24. A process of producing a compound of the formula

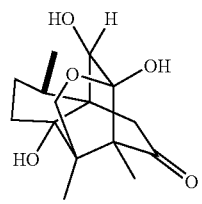

comprising b) reacting a compound of the formula

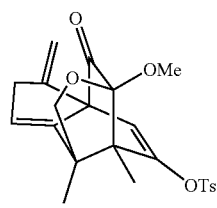

with $NaBH_4$ and MeOH to produce a compound of the formula

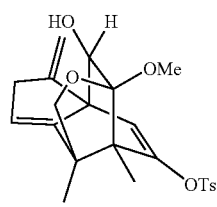

b) reacting the product of step a) with TMS-Imid to produce a compound of the formula

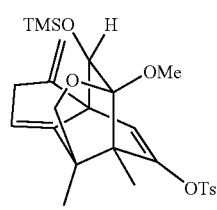

c) reacting the product of step b) with mCPBA and DCM to produce a compound of the formula
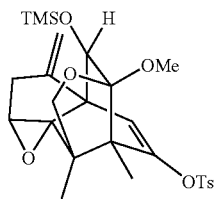
d) reacting the product of step c) with H₂, Pd/C 5%, and EtOAc to produce a compound of the formula
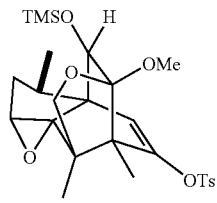
e) reacting the product of step d) with an acid in water to thereby obtain the compound.
* * * * *